(12) United States Patent
Hockfield et al.

(10) Patent No.: US 6,884,619 B2
(45) Date of Patent: Apr. 26, 2005

(54) INHIBITION OF BEHAB CLEAVAGE AND PRIMARY CENTRAL NERVOUS SYSTEM (CNS) TUMORS

(75) Inventors: Susan Hockfield, North Haven, CT (US); Russell T. Matthews, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 10/195,970

(22) Filed: Jul. 16, 2002

(65) Prior Publication Data

US 2003/0068661 A1 Apr. 10, 2003

Related U.S. Application Data

(60) Provisional application No. 60/306,046, filed on Jul. 17, 2001.

(51) Int. Cl.$^7$ .................................................. C12N 5/00
(52) U.S. Cl. ...................... 435/325; 435/6; 435/91.1; 435/375; 536/23.1; 536/24.1; 536/24.3; 536/24.33; 536/24.5
(58) Field of Search ................ 514/44; 435/6, 435/325, 91.1, 375; 536/24.1, 23.1, 24.3, 24.5

(56) References Cited

U.S. PATENT DOCUMENTS

| | | |
|---|---|---|
| 4,160,452 A | 7/1979 | Theeuwes |
| 4,256,108 A | 3/1981 | Theeuwes |
| 4,265,874 A | 5/1981 | Bonsen et al. |
| 4,683,195 A | 7/1987 | Mullis et al. |
| 4,683,202 A | 7/1987 | Mullis |
| 4,728,512 A | 3/1988 | Mehta et al. |
| 4,728,513 A | 3/1988 | Ventouras |
| 4,786,600 A | 11/1988 | Kramer et al. |
| 4,800,159 A | 1/1989 | Mullis et al. |
| 4,876,187 A | 10/1989 | Duck et al. |
| 5,011,769 A | 4/1991 | Duck et al. |
| 5,023,243 A | 6/1991 | Tullis |
| 5,084,287 A | 1/1992 | Ghebre-Sellassie et al. |
| 5,168,053 A | 12/1992 | Altman et al. |
| 5,190,931 A | 3/1993 | Inouye |
| 5,285,186 A | 2/1994 | Chen |
| 5,635,370 A | 6/1997 | Hockfield et al. |
| 6,180,370 B1 | 1/2001 | Queen et al. |

FOREIGN PATENT DOCUMENTS

WO    WO 87/02671    5/1987

OTHER PUBLICATIONS

Yamada et al. cDNA cloning and the identificationof an aggrecanase–like cleavage site in rat brevican. Biochemical and Biophysical Research Communications, 1995 vol. 216:957–963.*

Asperg et al. The c–type lectin domains of lecticans, a family of aggregating chondroitin sulfate proteoglycans, bind tenascin–R by protein–protein interactions independent of carbohydrate moiety. Proc. Natl. Acad. Sci., 1997 vol. 94:10116–10121.*

(Continued)

Primary Examiner—John L. LeGuyader
Assistant Examiner—Terra C. Gibbs
(74) Attorney, Agent, or Firm—Morgan, Lewis & Bockius, LLP

(57) ABSTRACT

The present invention relates to primary CNS tumors and provides useful compositions and methods for reducing tumor volume and increasing the length of survival in mammals with primary CNS tumors, thereby providing a treatment for primary CNS tumors. The invention also relates to methods of identifying compounds for reducing tumor volume and increasing animal survival, which therefore relate to treating primary CNS tumors.

14 Claims, 5 Drawing Sheets

OTHER PUBLICATIONS

Zhang et al. The G3 domain of versican inhibits mesenchymal chondrogenesis via the epidermal growtn factor–like motifs. Journal of Biological Chemistry, 1998 vol. 273:33054–33063.*

Yamada, H. et al., "*cDNA Cloning And The Identification Of An Aggrecanase–Like Cleavage Site In Rat Brevican,*" Biochemical And Biophysical Research Communications, vol. 216, No. 3, pp. 957–963 (Nov. 22, 1995).

Ausubel et al., 1997, Current Protocols in Molecular Biology, John Wiley & Sons, New York.

Barbas, Synthetic Human Antibodies, Nature Medicine, vol. 1, No. 8, pps. 837–839, Aug., 1995.

Bartel et al., The Yeast Two–Hybrid System, Oxford University Press, Cary, NC.

Beerli et al., Inhibition of Signaling From Type 1 Receptor Tyrosine Kinases via Intracellular Expression of Single–Chain Antibodies, Breast Cancer Research and Treatment, 38: 11–17, 1996 Kluwer Academic Publishers, Netherlands.

Bej et al., Polymerase Chain Reaction–Gene Probe Detection of Microorganisms by Using Filter–Concentrated Samples, Applied and Environmental Microbiology, vol. 57, No. 12, pps. 3529–3534, Dec. 1991.

Beychok, Cells of Immunoglobulin Synthesis, Academic Press, New York, 1979.

Bird et al., Single–Chain Antigen–Binding Proteins, Science vol. 242, pp. 423–426, Oct., 1988.

Blais, Burton W., Transcriptional Enhancement of the *Listeria Monocytogenes* PCR and Simple Immunoenzymatic Assay of the Product Using Anti–RNA:DNA Antibodies, Applied and Environmental Microbiology, vol. 60, No. 1, pps. 348–352, Jan., 1994.

Bodansky et al., The Practice of Peptide Synthesis, 1984, Springer–Verlag, New York.

Burton et al., Human Antibodies from Combinatorial Libraries, Advances in Immunology, vol. 57 pp. 191–280, 1994.

Cech, Thomas R., Ribozymes and Their Medical Implications, J. Amer. Med. Assn. vol. 260, No. 20, pps. 3030–3034, Nov., 25, 1988.

Cech et al., RNA Catalysis by a Group 1 Ribozyme, The Journal of Biol. Chem. vol. 267No. 25, pps. 17479–17482, The American Society for Biochemistry and Molecular Biology, Inc., Printed in U.S.A.

Cohen, 1989, In: Oligodeoxyribonucleotides, Antisense Inhibitors of Gene Expression, CRC Press, Boca Raton, FL.

DeClerk et al., Inhibition of Tumor Invasion of Smooth Muscle Cell Layers by Recombinant Human Metalloproteinase Inhibitor, Cancer Research 51: 2151–2157, Apr. 15, 1991.

De Kruif et al., Selection and Application of Human Single Chain Fv Antibody Fragments From a Semi–Synthetic Phage Antibody Display Library With Designed CDR3 Regions, J. Mol. Biol. 248: 97–105, 1995, Academic Press Limited.

Delpech et al., The Origin of Hyaluronectin in Human Tumors, International Journal of Cancer vol. 72, 942–948, 1997 Wiley–Liss, Inc.

Deryugina et al., Matrix Metalloproteinase–2 Activation Modulates Glioma Cell Migration, Journal of Cell Science 110: 2473–2482, Printed in Great Britain © The Company of Biologists Limited, 1997.

Duplaa et al., Quantitative Analysis of Polymerase Chain Reaction Products Using Biotinylated dUTP Incorporation, Anal. Biochem. 212: 229–236, © 1993 by Academic Press, Inc.

Forsyth et al., Gelatinase–A (MMP–2), Gelatinase–B (MMP–9) and Membrane Type Matrix Metalloproteinase–1 (MT1–MMP) are Involved in Different Aspects of the Pathophysiuology of Malignant Gliomas, British Journal of Cancer 79: 1828–1835, © 1999 Cancer Research Campaign.

Fosang et al., Generation and Novel Distribution of Matrix Metalloproteinase–derived Aggrecan Fragments in Porcine Cartilage Explants, J. Biol. Chem., 275: 33027–33037, 2000 © 2000 by The American Society for Biochemistry and Molecular Biology, Inc.

Furcht et al., Tumor Cell Invasion, Matrix Metalloproteinases, and the Dogma, Laboratory Investigation 70: 781–783, © 1994 The United States and Canadian Academy of Pathology, Inc.

Gary et al., BEHAB/Brevican: A Brain–Specific Lectican Implicated in Gliomas and Glial Cell Motility, 2000, Gene 2356: 139–147.

Genaro et al., 1985, Remington's Pharmaceutical Sciences, Mack Publishing Co., Easton, PA.

Gillam et al., Site–Specific Mutagenesis Using Synthetic Oligodeoxyribonucleotide Primers: I. Optimum Conditions and Minimum Oligodeoxyribonucleotide Length, Gene, vol. 8 pp. 81–97, 1979, Elsevier/North–Holland Biomedical Press.

Goldbrunner et al., Cell–Extracellular Matrix Interaction in Glioma Invasion, Acta Neurochirurgica 141:295–305, © Springer–Verlag 1999, printed in Austria.

Gu et al., Construction and Expression of Mouse–Human Chimeric Antibody SZ–51 Specific for Activated Platelet P–Selectin, 1997, Thrombosis and Hematocyst 77: 755–759.

Hall et al., Hyaluronan: RHAMM Mediated Cell Locomotion and signaling in Tumorigenesis, Journal of Neuro–Oncology 26:221–229, © 1995 Kluwer Academic Publishers, printed in the Netherlands.

Hall et al., Overexpression of the Hyaluronan Receptor RHAMM is Transforming and is Also Required for H–ras Transformation, Cell 82: 19–28, © 1995 by Cell Press.

Hamasuna et al., Regulation of Matrix Metalloproteinase–2 (MMP–2) by Hepatocyte Growth Factor/Scatter Factor (HGF/SF) in Human Glioma Cells: HGF/SF Enhances MMP–2 Expression and Activation Accomanying Up–Regulation of Membrane Type–1 MMP, International Journal of Cancer 82: 274–281 © 1999 Wiley–Liss, Inc.

Hampel et al., RNA Catalytic Properties of the Minimum (–)s TRSV Sequence, Biochemistry 28: 4929–4933, © 1989 American Chemical Society.

Harlow et al., 1988, Using Antibodies: A Laboratory Manual, Cold Spring Harbor Laboratory Press, NY.

Heath et al., Clinical Potential of Matrix Metalloprotease Inhibitors in Cancer Therapy, Drugs 59: 1043–1055, © Adis International Limited, May, 2000.

Higuchi et al., Kinetic PCR Analysis: Real–Time Monitoring of DNA Amplification Reactions, Bio/Technology 11: 1026–1030, Sep., 1993.

Hockfield, Proteoglycans in Neural Development, Semin. Dev. Biol. 1:55–63, © 1990 by W.B. Saunders Company.

Huston et al., Protein Engineering of Antibody Binding Sites: Recovery of Specific Activity in an Anti–Digoxin Single–Chain Fv Analogue Produced in *Escherichia coli*, Proc. Natl. Acad. Sci. USA 85: 5879–5883, Aug., 1988.

Iida et al., Rapid and Sensitive Method for Detection of Salmonella Strains Using a Combination of Polymerase Chain Reaction and Reverse Dot–blot hybridization, FEMS Microbiol. Lett. 114: 167–172, © 1993 Federation of European Microbiological Societies.

Jaworski et al., BEHAB, a New Member of the Proteoglycan Tandem Repeat Family of Hyaluronan–binding Proteins That is Restricted to the Brain, J. Cell Biol. 125: 495–509, © The Rockefeller University Press, Apr., 1994.

Jaworski et al., BEHAB (Brain Enriched Hyaluronan Binding) is Expressed in Surgical Samples of Glioma and in Intgracranial Grafts of Invasive Glioma Cell Lines, Cancer Research, vol. 56, No. 10, pp. 2293–2298, May, 1996.

Kazmierski, 1999, Peptidomimetics Protocols, Methods in Molecular Medicine, vol. 23, Humana Press, Totowa, NJ.

Kosaki et al., Overproduction of Hyaluronan by Expression of the Hyaluronan Synthase Has2 Enhances Anchorage–independent Growth and Tumorigenicity, Cancer Research, 59: 1141–1145, March, 1999.

Kramer et al., Replicatable RNA Reporters, Nature 339: 401–402, Jun. 1, 1989.

Laemmli et al., Clevage of Structural Proteins During the Assembly of the Head of Bacteriophage T4, Nature 227: 680–685, Aug. 15, 1970.

Lizardi et al., Exponential Amplification of Recombinant–RNA Hybridization Probes, Bio/Technology 6: 1197–1202, Oct., 1988.

Lomeli et al., Quantitative Assays Based on the Use of Replicatable Hybridization Probes, Clinical Chem. 35: 1826–1831, 1989.

Marcus–Sekura, Techniques for Using Antisense Oligodeoxyribonucleotides to Study Gene Expression, Anal. Biochem. 172: 289, 1988.

Marks et al., Human Antibodies from V–gene Libraries Displayed on Phage, J Mol. Biol. 222: 581–597, 1991, Academic Press Limited.

Martel–Pelletier et al., Metalloproteases and Inhibitors in Arthritic Diseases, Best Pract. Res. Clin. Rheumatol., 15: 805–29, © 2001 Harcourt Publishers Ltd.

Matthews et al., Brain–Enriched Hyaluronan Binding (BEHAB) Brevican Cleavage in a Glioma Cell Line is Mediated by a Disintegrin and Metalloproteinase with Thrombospondin Motifs, The Journal of Biological Chemistry, vol. 275, No. 30, pp. 22695–22703, Jul., 2000, The American Society for Biochemistry and Molecular Biology, Inc., Printed in USA.

Merzak et al., CD44 Mediates Human Glioma Cell Adhesion and Invasion in Vitro,, Cancer Research 54: 3988–3992, Aug. 1, 1994.

Mignatti et al., Biology and Biochemistry of Proteinases in Tumor Invasion, Physiological Reviews 73: 161–195, © Jan., 1993, The American Physiological Society.

Mohanam et al., Proteolysis and Invasiveness of Brain Tumors: Role of Urokinase–type plasminogen Activator Receptor, Journal of Neuro–Oncology, 22: 153–160, © 1994 Kluwer Academic Publishers, Printed in the Netherlands.

Nakagawa et al., Production of Matrix Metalloproteinases and Tissue Inhibitor of Metalloproteinases–1 by Human Brain Tumors, Journal of Neurosurgery 81: 69–77, Jul., 1994.

Rao et al., Elevated Levels of $M_r$92,000 Type IV Collagenase in Human Brain Tumors, Cancer Research 53: 2208–2211, May 15, 1993.

Rao et al., Role of Plasminogen Activator and of 92 Kda Type IV Collagenase in Glioblastoma Invasion Using an in vitro matrigel model, Journal of Neuro–Oncology, 18: 129–138, © 1994 Kluwer Academic Publishers, Printed in the Netherlands.

Rao et al., Expression and Localization of 92 kDa Type IV Collagenase/Gelatinase B (MMP–9) in Human Gliomas, Clinical and Experimental Metastasis, 14: 12–18, © 1996 Rapid Science Publishers.

Roberts, et al., Generation of an Antibody With Enhanced Affinity and Specificity for Its Antigen by Protein Engineering, Nature, vol. 328, pp, 731–734, Aug., 1987.

Rosen et al., Brain Volume Estimation from Serial Section Measurements: A Comparison of Methodologies, Journal of Neuroscience Methods 35: 115–124, © 1990 Elsevier Science Publisher B.V.

Sambrook et al., 1989, Molecular Cloning: A Laboratory Manual, Cold Spring Harbor Laboratory Press, New York.

Sawaya et al., Expression and Localization of 72 kDa Type IV Collagenase (MMP–2) in Human Malignant Gliomas in vivo, Clinical and Experimental Metastasis 14: 35–42, 1996.

Seidenbecher et al., Brevican, a Chondroitin Sulfate Proteoglycan of Rat Brain, Occurs as Secreted and Cell Surface Glycosylphosphatidylinositol–Anchored Isoforms, J. Biol. Chem. 270: 27206–27212, Nov., 1995, Printed in USA.

Stetler–Stevenson et al., Extracellular Matrix G: Role of Matrix Metalloproteinases in Tumor Invasion and Metastasis, FASEB Journal 7: 1434–1441, 1993.

Stewart et al. Solid Phase Peptide Synthesis, 2nd Edition, 1984, Pierce Chemical Company, Rockford, Illinois.

Streit, Wolfgang J., Microglial Response to Brain Injury: A Brief Synopsis, Toxicol. Pathol., 28: 28–30, © 2000 by the Society of Toxicologic Pathologists.

Towbin et al., Electrophoretic Transfer of Proteins From Polyacrylamide Gels to Nitrocellulose Sheets: Procedure and Some Applications, Proc. Natl. Acad. Sci. U.S.A., 76: 4350–4354, Sep. 1979.

Turley, Hyaluronan and Cell Locomotion, Cancer and Metastasis Reviews, 11:21–30, © 1992 Kluwer Academic Publishers, printed in the Netherlands.

Tuszynski et al., Thrombospondin Promotes Platelet Aggregation, Blood, vol. 72: pp. 109–115, Jul., 1988.

Tzanakakis Proteoglycan Synthesis Induced by Transforming and Basic Fibroblast Growth Factors in Human Malignant Mesothelioma is Mediated Through Sspecific Receptors and the Tyrosine Kinase Intracellular Pathway, 1997, Biochimie, 79:3230332, © Societe francaise de biochimie et biologie moleculaire/Elsevier, Paris, 1997.

Uhm et al., Glioma Invasion in vitro: Regulation by Matrix Metalloprotease–2 and Protein Kinase C, Clinical and Experimental Metastasis 14: 421–433, 1996, Rapid Science Publishers.

Vaithilingham et al., Serum Proteolytic Activity During the Growth of C6 Astrocytoma, Journal of Neurosurgery 77: 595–600, Oct., 1992.

Wright et al., Genetically Engineered Antibodies: Progress and Prospects, Critical Reviews in Immunology, vol. 12 pp. 125–168, 1992, CRC Press, Inc.

Yamada et al., Molecular Cloning of Brevican, a Novel Brain Proteoglycan of the Aggrecan/Versican Family, J. Biol. Chem. 269: 10119–10126, © 1994 by The American Society for Biochemistry and Molecular Biology, Inc.

Yamamoto et al., Activities, Localizations, and Roles of Serine Proteases and Their Inhibitors in Human Brain Tumor Progression, Journal of Neuro–Oncology, 22: 139–151, © 1994 Kluwer Academic Publishers, printed in the Netherlands.

Zetter, Adhesion Molecules in Tumor Metastasis, Seminars in Cancer Biology 4:219–229, © 1993 Academic Press Ltd.

Zhang et al., Expression of a Cleaved Brain–Specific Extracellular Matrix Protein Mediates Glioma Cell Invasion In Vivo, Journal of Neuroscience vol. 18, pp, 2370–2376, Apr., 1998.

* cited by examiner

CNS-1-
GFP

CNS-1-
FL

CNS-1-
NVY

SEQUENCE LISTING

```
<160> NUMBER OF SEQ ID NOS: 6

<210> SEQ ID NO 1
<211> LENGTH: 6
<212> TYPE: PRT
<213> ORGANISM: Rattus sp.

<400> SEQUENCE: 1

Glu Ser Glu Ser Arg Gly
1               5

<210> SEQ ID NO 2
<211> LENGTH: 6
<212> TYPE: PRT
<213> ORGANISM: Rattus sp.

<400> SEQUENCE: 2

Glu Ser Glu Asn Val Tyr
1               5

<210> SEQ ID NO 3
<211> LENGTH: 883
<212> TYPE: PRT
<213> ORGANISM: Rattus sp.

<400> SEQUENCE: 3

Met Ile Pro Leu Leu Leu Ser Leu Leu Ala Ala Leu Val Leu Thr Gln
1               5                   10                  15

Ala Pro Ala Ala Leu Ala Asp Asp Leu Lys Glu Asp Ser Ser Glu Asp
                20                  25                  30

Arg Ala Phe Arg Val Arg Ile Gly Ala Ala Gln Leu Arg Gly Val Leu
            35                  40                  45

Gly Gly Ala Leu Ala Ile Pro Cys His Val His His Leu Arg Pro Pro
        50                  55                  60
```

```
Pro Ser Arg Arg Ala Ala Pro Gly Phe Pro Arg Val Lys Trp Thr Phe
 65                  70                  75                  80

Leu Ser Gly Asp Arg Glu Val Glu Val Leu Val Ala Arg Gly Leu Arg
                 85                  90                  95

Val Lys Val Asn Glu Ala Tyr Arg Phe Arg Val Ala Leu Pro Ala Tyr
                100                 105                 110

Pro Ala Ser Leu Thr Asp Val Ser Leu Val Leu Ser Glu Leu Arg Pro
            115                 120                 125

Asn Asp Ser Gly Val Tyr Arg Cys Glu Val Gln His Gly Ile Asp Asp
130                 135                 140

Ser Ser Asp Ala Val Glu Val Lys Val Lys Gly Val Val Phe Leu Tyr
145                 150                 155                 160

Arg Glu Gly Ser Ala Arg Tyr Ala Phe Ser Phe Ala Gly Ala Gln Glu
                165                 170                 175

Ala Cys Ala Arg Ile Gly Ala Arg Ile Ala Thr Pro Glu Gln Leu Tyr
            180                 185                 190

Ala Ala Tyr Leu Gly Gly Tyr Glu Gln Cys Asp Ala Gly Trp Leu Ser
            195                 200                 205

Asp Gln Thr Val Arg Tyr Pro Ile Gln Asn Pro Arg Glu Ala Cys Tyr
            210                 215                 220

Gly Asp Met Asp Gly Tyr Pro Gly Val Arg Asn Tyr Gly Val Val Gly
225                 230                 235                 240

Pro Asp Asp Leu Tyr Asp Val Tyr Cys Tyr Ala Glu Asp Leu Asn Gly
                245                 250                 255

Glu Leu Phe Leu Gly Ala Pro Gly Lys Leu Thr Trp Glu Glu Ala
            260                 265                 270

Arg Asp Tyr Cys Leu Glu Arg Gly Ala Gln Ile Ala Ser Thr Gly Gln
            275                 280                 285

Leu Tyr Ala Ala Trp Asn Gly Gly Leu Asp Arg Cys Ser Pro Gly Trp
290                 295                 300

Leu Ala Asp Gly Ser Val Arg Tyr Pro Ile Ile Thr Pro Ser Gln Arg
305                 310                 315                 320

Cys Gly Gly Gly Leu Pro Gly Val Lys Thr Leu Phe Leu Phe Pro Asn
                325                 330                 335

Gln Thr Gly Phe Pro Ser Lys Gln Asn Arg Phe Asn Val Tyr Cys Phe
            340                 345                 350

Arg Asp Ser Ala His Pro Ser Ala Phe Ser Glu Ala Ser Ser Pro Ala
            355                 360                 365

Ser Asp Gly Leu Glu Ala Ile Val Thr Val Thr Glu Lys Leu Glu Glu
370                 375                 380

Leu Gln Leu Pro Gln Glu Ala Val Glu Ser Glu Asn Val Tyr Ala Ile
385                 390                 395                 400

Tyr Ser Ile Pro Ile Thr Glu Asp Gly Gly Gly Ser Ser Thr Pro
                405                 410                 415

Glu Asp Pro Ala Glu Ala Pro Arg Thr Pro Leu Glu Ser Glu Thr Gln
                420                 425                 430

Ser Val Ala Pro Pro Thr Gly Ser Ser Glu Glu Glu Gly Glu Ala Leu
            435                 440                 445

Glu Glu Glu Glu Arg Phe Lys Asp Thr Glu Thr Pro Lys Glu Glu Lys
            450                 455                 460

Glu Gln Glu Asn Leu Trp Val Trp Pro Thr Glu Leu Ser Ser Pro Leu
465                 470                 475                 480
```

```
Pro Thr Gly Leu Glu Thr His Ser Leu Ser Gln Val Ser Pro Pro
            485                 490                 495

Ala Gln Ala Val Leu Gln Leu Gly Ala Ser Pro Ser Pro Arg Pro Pro
            500                 505                 510

Arg Val His Gly Pro Pro Ala Glu Thr Leu Gln Pro Pro Arg Glu Gly
            515                 520                 525

Ser Leu Thr Ser Thr Pro Asp Gly Ala Arg Glu Val Ala Gly Glu Thr
            530                 535                 540

Gly Ser Pro Glu Leu Ser Gly Val Pro Arg Glu Ser Glu Glu Ala Gly
545                 550                 555                 560

Ser Ser Ser Leu Glu Asp Gly Pro Ser Leu Leu Pro Ala Thr Trp Ala
                565                 570                 575

Pro Val Gly Thr Arg Glu Leu Glu Thr Pro Ser Glu Glu Lys Ser Gly
            580                 585                 590

Arg Thr Val Leu Thr Gly Thr Ser Val Gln Ala Gln Pro Val Leu Pro
            595                 600                 605

Thr Asp Ser Ala Ser Arg Gly Gly Val Ala Val Ala Pro Ser Ser Gly
            610                 615                 620

Asp Cys Ile Pro Ser Pro Cys His Asn Gly Gly Thr Cys Leu Glu Glu
625                 630                 635                 640

Lys Glu Gly Phe Arg Cys Leu Cys Leu Pro Gly Tyr Gly Gly Asp Leu
                645                 650                 655

Cys Asp Val Gly Leu His Phe Cys Ser Pro Gly Trp Glu Ala Phe Gln
                660                 665                 670

Gly Ala Cys Tyr Lys His Phe Ser Thr Arg Arg Ser Trp Glu Glu Ala
            675                 680                 685

Glu Ser Gln Cys Arg Ala Leu Gly Ala His Leu Thr Ser Ile Cys Thr
            690                 695                 700

Pro Glu Glu Gln Asp Phe Val Asn Asp Arg Tyr Arg Glu Tyr Gln Trp
705                 710                 715                 720

Ile Gly Leu Asn Asp Arg Thr Ile Glu Gly Asp Phe Leu Trp Ser Asp
                725                 730                 735

Gly Ala Pro Leu Leu Tyr Glu Asn Trp Asn Pro Gly Gln Pro Asp Ser
            740                 745                 750

Tyr Phe Leu Ser Gly Glu Asn Cys Val Val Met Val Trp His Asp Gln
            755                 760                 765

Gly Gln Trp Ser Asp Val Pro Cys Asn Tyr His Leu Ser Tyr Thr Cys
770                 775                 780

Lys Met Gly Leu Val Ser Cys Gly Pro Pro Gln Leu Pro Leu Ala
785                 790                 795                 800

Gln Ile Phe Gly Arg Pro Arg Leu Ala Tyr Ala Val Asp Thr Val Leu
            805                 810                 815

Arg Tyr Arg Cys Arg Asp Gly Leu Ala Gln Arg Asn Leu Pro Leu Ile
            820                 825                 830

Arg Cys Gln Glu Asn Gly Leu Trp Glu Ala Pro Gln Ile Ser Cys Val
            835                 840                 845

Pro Arg Arg Pro Ala Arg Ala Leu Arg Ser Met Thr Ala Pro Glu Gly
            850                 855                 860

Pro Arg Gly Gln Leu Pro Arg Gln Arg Lys Ala Leu Leu Thr Pro Pro
865                 870                 875                 880

Ser Ser Leu

<210> SEQ ID NO 4
```

-continued

```
<211> LENGTH: 2652
<212> TYPE: DNA
<213> ORGANISM: Rattus sp.

<400> SEQUENCE: 4
atgatcccat tgcttctgtc cctgctggca gctctggtcc tgacccaagc ccctgcagcc      60
ctcgctgatg acctgaaaga agacagctca gaggatcgag cctttcgggt gcgcatcggt     120
gccgcgcagc tgcggggtgt gctgggcggt gccctggcca tcccatgcca cgtccaccac     180
ctgaggccgc cgcccagccg ccgggccgcg ccgggctttc ccgagtcaa atggaccttc      240 ctgtccgggg accgggaggt ggaggtgctg gtggcgcgcg gctgcgcgt caaggtaaac      300 gaagcctatc ggttccgcgt ggcgctgcct gcctaccccg catcgctcac agatgtgtct     360
ttagtattga gcgaactgcg gcccaatgat tccggggtct atcgctgcga ggtccagcac     420
ggtatcgacg acagcagtga tgctgtggaa gtcaaggtca aggggtcgt cttcctctac      480 cgagagggct ctgcccgcta tgctttctcc ttcgctggag cccaggaagc ctgtgctcgc     540
atcggagccc gaattgccac ccctgagcag ctgtatgctg cctacctcgg cggctatgaa     600
cagtgtgatg ctggctggct gtccgaccaa accgtgaggt accccatcca gaacccacga     660
gaagcctgtt atggagacat ggatggctac cctggagtgc ggaattacgg agtggtgggt     720
cctgatgatc tctacgatgt ctactgttat gccgaagacc taaatggaga actgttccta     780
ggtgcccctc ccggcaagct gacgtgggag gaggctcggg actactgtct ggaacgcggt     840
gctcagatcg ctagcacggg ccagctatac gcggcatgga atggcggctt ggacagatgt     900
agccctggct ggctggctga tggcagtgtg cggtacccca tcatcacgcc cagccaacgc     960
tgtgggggag gctgccagg agtcaagacc ctcttcctct ttcccaacca gactggcttc     1020
cccagcaagc agaaccgctt caatgtctac tgcttccgag actctgccca tccctctgcc     1080
ttctctgagg cctccagccc agcctctgat ggactagagg ccattgtcac agtgacagag     1140
aagctggagg aactgcagtt gcctcaggaa gctgtggaga gcgagaatgt ttacgcgatc     1200
tactccatcc ccatcacaga agatggggga ggaggaagct ctaccccaga gacccagca      1260 gaggccccca ggactcctct agaatcagaa acccaatccg ttgcaccacc taccgggtcc     1320
tcagaagagg aaggcgaagc cctggaggaa gagaaagat tcaaagacac agagactccg      1380
aaggaagaga aggagcagga gaacctgtgg gtgtggccca cggagctcag cagccctctc     1440
cctactggct tggaaacaga gcactcactc tcccaggtgt ccccaccagc ccaggcagtt     1500
ctacagctgg gtgcatcacc ttctcccagg cctccaaggg tccatggacc gctgcagag      1560 actttgcaac ccccaaggga gggaagcctc acatctactc cagatggggc aagagaagta     1620
gcgggggaaa ctgggagccc tgagctctct ggggttcctc gagaaagcga ggaggcagga     1680
agctccagct tggaggatgg cccttccctc cttccagcga catgggcccc tgtgggtacc     1740
agggagctga gaccccctc agaagagaag tctggaagaa ctgttctgac aggcacatca     1800
gtgcaggccc agccagtgct gcccaccgac agtgccagcc gaggtggagt ggctgtggct     1860
ccctcatcag gtgactgtat ccccagcccc tgccacaatg gtgggacatg cttggaggag     1920
aaggagggtt tccgctgcct ctgtttgcca ggctatgggg gggacctgtg cgatgttggc     1980
ctccacttct gcagcccggg ctgggaggcc ttccaggtg cctgctacaa gcacttttcc      2040
acacgaagga gttggggagga ggcagaaagc cagtgccgag cgctagggc tcatctgacc     2100 agcatctgca cccctgagga gcaggacttt gtcaacgatc gatacaggga gtaccagtgg     2160
attgggctca atgacaggac catcgagggt gacttcctgt ggtcagatgg tgcccctctg     2220
```

-continued

| | |
|---|---|
| ctctatgaaa actggaaccc tgggcagcct gacagctact tcctgtctgg ggagaactgt | 2280 |
| gtggtcatgg tgtggcatga ccagggacag tggagtgatg taccctgcaa ctaccaccta | 2340 |
| tcctacacct gcaagatggg gcttgtgtca tgtggacctc caccacagct gcccctggct | 2400 |
| caaatatttg gtcgccctcg gctggcctac gcggtggaca ctgtgcttcg atatcggtgc | 2460 |
| cgagacgggc tggcccagcg caacttgccg ttgatccgct gccaggagaa tgggctttgg | 2520 |
| gaggcccctc agatttcttg cgtgccccga agacctgccc gtgctctccg ctcaatgacc | 2580 |
| gccccagaag gaccacgggg acagctcccg aggcagagga agcactgtt gacacctccc | 2640 |
| tccagtctct ag | 2652 |

<210> SEQ ID NO 5
<211> LENGTH: 2652
<212> TYPE: DNA
<213> ORGANISM: Rattus sp.

<400> SEQUENCE: 5

| | |
|---|---|
| atgatcccat tgcttctgtc cctgctggca gctctggtcc tgacccaagc ccctgcagcc | 60 |
| ctcgctgatg acctgaaaga agacagctca gaggatcgag cctttcgggt gcgcatcggt | 120 |
| gccgcgcagc tgcggggtgt gctgggcggt gccctggcca tcccatgcca cgtccaccac | 180 |
| ctgaggccgc cgcccagccg ccgggccgcg ccgggctttc cccgagtcaa atggaccttc | 240 |
| ctgtccgggg accgggaggt ggaggtgctg gtggcgcgcg ggctgcgcgt caaggtaaac | 300 |
| gaagcctatc ggttccgcgt ggcgctgcct gcctaccccg catcgctcac agatgtgtct | 360 |
| ttagtattga gcgaactgcg gcccaatgat tccggggtct atcgctgcga ggtccagcac | 420 |
| ggtatcgacg acagcagtga tgctgtggaa gtcaaggtca aggggtcgt cttcctctac | 480 |
| cgagagggct ctgcccgcta tgcttctcc ttcgctggag cccaggaagc ctgtgctcgc | 540 |
| atcggagccc gaattgccac ccctgagcag ctgtatgctg cctacctcgg cggctatgaa | 600 |
| cagtgtgatg ctggctggct gtccgaccaa accgtgaggt accccatcca gaacccacga | 660 |
| gaagcctgtt atggagacat ggatggctac cctggagtgc ggaattacgg agtggtgggt | 720 |
| cctgatgatc tctacgatgt ctactgttat gccgaagacc taaatggaga actgttccta | 780 |
| ggtgccctc ccggcaagct gacgtgggag gaggctcggg actactgtct ggaacgcggt | 840 |
| gctcagatcg ctagcacggg ccagctatac gcggcatgga atggcggctt ggacagatgt | 900 |
| agccctggct ggctggctga tggcagtgtg cggtacccca tcatcacgcc agccaacgc | 960 |
| tgtggggggag gcctgccagg agtcaagacc ctcttcctct ttcccaacca gactggcttc | 1020 |
| cccagcaagc agaaccgctt caatgtctac tgcttccgag actctgccca tccctctgcc | 1080 |
| ttctctgagg cctccagccc agcctctgat ggactagagg ccattgtcac agtgacagag | 1140 |
| aagctggagg aactgcagtt gcctcaggaa gctgtggaga gcagtctcg tggggcgatc | 1200 |
| tactccatcc ccatcacaga agatggggga ggaggaagct ctaccccaga agacccagca | 1260 |
| gaggccccca ggactcctct agaatcagaa acccaatccg ttgcaccacc taccgggtcc | 1320 |
| tcagaagagg aaggcgaagc cctggaggaa gaagaaagat tcaaagacac agagactccg | 1380 |
| aaggaagaga aggagcagga gaacctgtgg gtgtggccca ggagctcag cagccctctc | 1440 |
| cctactggct tggaaacaga gcactcactc tcccaggtgt ccccaccagc ccaggcagtt | 1500 |
| ctacagctgg gtgcatcacc ttctcccagg cctccaaggg tccatggacc gcctgcagag | 1560 |
| actttgcaac ccccaaggga gggaagcctc acatctactc cagatggggc aagagaagta | 1620 |

-continued

```
gcgggggaaa ctgggagccc tgagctctct ggggttcctc gagaaagcga ggaggcagga    1680
agctccagct tggaggatgg cccttccctc cttccagcga catgggcccc tgtgggtacc    1740
agggagctgg agacccctc agaagagaag tctggaagaa ctgttctgac aggcacatca     1800
gtgcaggccc agccagtgct gcccaccgac agtgccagcc gaggtggagt ggctgtggct    1860
ccctcatcag gtgactgtat ccccagcccc tgccacaatg gtgggacatg cttggaggag    1920
aaggagggtt tccgctgcct ctgtttgcca ggctatgggg gggacctgtg cgatgttggc    1980
ctccacttct gcagcccggg ctgggaggcc ttccagggtg cctgctacaa gcacttttcc    2040
acacgaagga gttgggagga ggcagaaagc cagtgccgag cgctaggggc tcatctgacc    2100
agcatctgca cccctgagga gcaggacttt gtcaacgatc gatacaggga gtaccagtgg    2160
attgggctca atgacaggac catcgagggt gacttcctgt ggtcagatgg tgccctctg     2220 ctctatgaaa actggaaccc tgggcagcct gacagctact tcctgtctgg ggagaactgt    2280
gtggtcatgg tgtggcatga ccagggacag tggagtgatg taccctgcaa ctaccaccta    2340
tcctacacct gcaagatggg gcttgtgtca tgtggacctc caccacagct gccctggct    2400 caaatatttg gtcgccctcg gctggcctac gcggtggaca ctgtgcttcg atatcggtgc    2460
cgagacgggc tggcccagcg caacttgccg ttgatccgct gccaggagaa tgggctttgg    2520
gaggcccctc agatttcttg cgtgccccga agacctgccc gtgctctccg ctcaatgacc    2580
gccccagaag gaccacgggg acagctcccg aggcaggaga agcactgtt gacacctccc      2640 tccagtctct ag                                                        2652
```

<210> SEQ ID NO 6
<211> LENGTH: 883
<212> TYPE: PRT
<213> ORGANISM: Rattus sp.

<400> SEQUENCE: 6

```
Met Ile Pro Leu Leu Ser Leu Leu Ala Leu Val Leu Thr Gln
1               5                   10                  15

Ala Pro Ala Ala Leu Ala Asp Asp Leu Lys Glu Asp Ser Ser Glu Asp
            20                  25                  30

Arg Ala Phe Arg Val Arg Ile Gly Ala Ala Gln Leu Arg Gly Val Leu
        35                  40                  45

Gly Gly Ala Leu Ala Ile Pro Cys His Val His His Leu Arg Pro Pro
    50                  55                  60

Pro Ser Arg Arg Ala Ala Pro Gly Phe Pro Arg Val Lys Trp Thr Phe
65                  70                  75                  80

Leu Ser Gly Asp Arg Glu Val Glu Val Leu Val Ala Arg Gly Leu Arg
                85                  90                  95

Val Lys Val Asn Glu Ala Tyr Arg Phe Arg Val Ala Leu Pro Ala Tyr
            100                 105                 110

Pro Ala Ser Leu Thr Asp Val Ser Leu Val Leu Ser Glu Leu Arg Pro
        115                 120                 125

Asn Asp Ser Gly Val Tyr Arg Cys Glu Val Gln His Gly Ile Asp Asp
    130                 135                 140

Ser Ser Asp Ala Val Glu Val Lys Val Lys Gly Val Val Phe Leu Tyr
145                 150                 155                 160

Arg Glu Gly Ser Ala Arg Tyr Ala Phe Ser Phe Ala Gly Ala Gln Glu
                165                 170                 175

Ala Cys Ala Arg Ile Gly Ala Arg Ile Ala Thr Pro Glu Gln Leu Tyr
            180                 185                 190
```

-continued

```
Ala Ala Tyr Leu Gly Gly Tyr Glu Gln Cys Asp Ala Gly Trp Leu Ser
        195                 200                 205

Asp Gln Thr Val Arg Tyr Pro Ile Gln Asn Pro Arg Glu Ala Cys Tyr
        210                 215                 220

Gly Asp Met Asp Gly Tyr Pro Gly Val Arg Asn Tyr Gly Val Val Gly
225                 230                 235                 240

Pro Asp Asp Leu Tyr Asp Val Tyr Cys Tyr Ala Glu Asp Leu Asn Gly
                245                 250                 255

Glu Leu Phe Leu Gly Ala Pro Gly Lys Leu Thr Trp Glu Glu Ala
        260                 265                 270

Arg Asp Tyr Cys Leu Glu Arg Gly Ala Gln Ile Ala Ser Thr Gly Gln
        275                 280                 285

Leu Tyr Ala Ala Trp Asn Gly Gly Leu Asp Arg Cys Ser Pro Gly Trp
        290                 295                 300

Leu Ala Asp Gly Ser Val Arg Tyr Pro Ile Ile Thr Pro Ser Gln Arg
305                 310                 315                 320

Cys Gly Gly Gly Leu Pro Gly Val Lys Thr Leu Phe Leu Phe Pro Asn
                325                 330                 335

Gln Thr Gly Phe Pro Ser Lys Gln Asn Arg Phe Asn Val Tyr Cys Phe
        340                 345                 350

Arg Asp Ser Ala His Pro Ser Ala Phe Ser Glu Ala Ser Ser Pro Ala
        355                 360                 365

Ser Asp Gly Leu Glu Ala Ile Val Thr Val Thr Glu Lys Leu Glu Glu
        370                 375                 380

Leu Gln Leu Pro Gln Glu Ala Val Glu Ser Glu Ser Arg Gly Ala Ile
385                 390                 395                 400

Tyr Ser Ile Pro Ile Thr Glu Asp Gly Gly Gly Ser Ser Thr Pro
                405                 410                 415

Glu Asp Pro Ala Glu Ala Pro Arg Thr Pro Leu Glu Ser Glu Thr Gln
        420                 425                 430

Ser Val Ala Pro Pro Thr Gly Ser Ser Glu Glu Glu Gly Glu Ala Leu
        435                 440                 445

Glu Glu Glu Glu Arg Phe Lys Asp Thr Glu Thr Pro Lys Glu Glu Lys
450                 455                 460

Glu Gln Glu Asn Leu Trp Val Trp Pro Thr Glu Leu Ser Ser Pro Leu
465                 470                 475                 480

Pro Thr Gly Leu Glu Thr Glu His Ser Leu Ser Gln Val Ser Pro Pro
                485                 490                 495

Ala Gln Ala Val Leu Gln Leu Gly Ala Ser Pro Ser Pro Arg Pro Pro
            500                 505                 510

Arg Val His Gly Pro Pro Ala Glu Thr Leu Gln Pro Pro Arg Glu Gly
        515                 520                 525

Ser Leu Thr Ser Thr Pro Asp Gly Ala Arg Glu Val Ala Gly Glu Thr
        530                 535                 540

Gly Ser Pro Glu Leu Ser Gly Val Pro Arg Glu Ser Glu Glu Ala Gly
545                 550                 555                 560

Ser Ser Ser Leu Glu Asp Gly Pro Ser Leu Leu Pro Ala Thr Trp Ala
                565                 570                 575

Pro Val Gly Thr Arg Glu Leu Glu Thr Pro Ser Glu Glu Lys Ser Gly
        580                 585                 590

Arg Thr Val Leu Thr Gly Thr Ser Val Gln Ala Gln Pro Val Leu Pro
        595                 600                 605
```

-continued

```
Thr Asp Ser Ala Ser Arg Gly Val Ala Val Ala Pro Ser Ser Gly
    610             615             620

Asp Cys Ile Pro Ser Pro Cys His Asn Gly Gly Thr Cys Leu Glu Glu
625             630             635                     640

Lys Glu Gly Phe Arg Cys Leu Cys Leu Pro Gly Tyr Gly Gly Asp Leu
            645             650                 655

Cys Asp Val Gly Leu His Phe Cys Ser Pro Gly Trp Glu Ala Phe Gln
            660             665             670

Gly Ala Cys Tyr Lys His Phe Ser Thr Arg Arg Ser Trp Glu Glu Ala
            675             680             685

Glu Ser Gln Cys Arg Ala Leu Gly Ala His Leu Thr Ser Ile Cys Thr
    690             695             700

Pro Glu Glu Gln Asp Phe Val Asn Asp Arg Tyr Arg Glu Tyr Gln Trp
705             710             715             720

Ile Gly Leu Asn Asp Arg Thr Ile Glu Gly Asp Phe Leu Trp Ser Asp
                725             730             735

Gly Ala Pro Leu Leu Tyr Glu Asn Trp Asn Pro Gly Gln Pro Asp Ser
            740             745             750

Tyr Phe Leu Ser Gly Glu Asn Cys Val Val Met Val Trp His Asp Gln
        755             760             765

Gly Gln Trp Ser Asp Val Pro Cys Asn Tyr His Leu Ser Tyr Thr Cys
    770             775             780

Lys Met Gly Leu Val Ser Cys Gly Pro Pro Gln Leu Pro Leu Ala
785             790             795             800

Gln Ile Phe Gly Arg Pro Arg Leu Ala Tyr Ala Val Asp Thr Val Leu
            805             810             815

Arg Tyr Arg Cys Arg Asp Gly Leu Ala Gln Arg Asn Leu Pro Leu Ile
            820             825             830

Arg Cys Gln Glu Asn Gly Leu Trp Glu Ala Pro Gln Ile Ser Cys Val
        835             840             845

Pro Arg Arg Pro Ala Arg Ala Leu Arg Ser Met Thr Ala Pro Glu Gly
    850             855             860

Pro Arg Gly Gln Leu Pro Arg Gln Arg Lys Ala Leu Leu Thr Pro Pro
865             870             875             880

Ser Ser Leu
```

INHIBITION OF BEHAB CLEAVAGE AND PRIMARY CENTRAL NERVOUS SYSTEM (CNS) TUMORS

CROSS-REFERENCE TO RELATED APPLICATIONS

This application is entitled to priority pursuant to 35 U.S.C. §119(e) to U.S. Provisional Patent Application No. 60/306,046, filed on Jul. 17, 2001.

STATEMENT REGARDING FEDERALLY SPONSORED RESEARCH OR DEVELOPMENT

This invention was supported in part by funds obtained from the U.S. Government (National Institutes of Health Grant Numbers EY06511 and NS35228), and the U.S. Government may therefore have certain rights in the invention.

BACKGROUND OF THE INVENTION

Gliomas, primary brain tumors, are notoriously difficult to control and manage. Unlike secondary tumors that have metastasized to the brain or non-glial brain tumors, gliomas demonstrate a unique invasive ability, characterized by a lack of well-defined borders between cancerous tissue and healthy brain. Conventional therapies including surgery, chemotherapy, and radiation therapy, are often only partially effective or ineffective treatments due to the invasive nature of gliomas. Therefore, the prognosis of patients afflicted with gliomas is uniformly grim.

Not only is the prognosis often negative, but the diagnosis of gliomas is a difficult and costly process as well. Detection of brain tumors requires costly imaging equipment that is not readily available at all medical facilities, and confirmation of imaging results usually requires invasive and dangerous surgical sampling of the tumor.

The nature of the extracellular matrix (ECM) in the brain may play a role in the invasive capabilities of cancer cells. During normal development, the composition of the extracellular matrix of the brain changes dramatically. Cell proliferation, migration, neuronal and glial outgrowth and angiogenesis in the developing brain take place in a soluble matrix permissive to cell movement. In the mature, developed brain however, cell motility is markedly decreased to stabilize mature cell to cell interactions (Hockfield, 1990, Semin. Dev. Biol. 1:55–63).

The mechanisms employed by malignant tumors to invade the surrounding tissue in the developed brain differ remarkably. For example, some malignant cells are capable of producing their own ECM molecules, such as hyaluronic acid (HA), thereby changing the balance and structure of the neighboring environment (Delpech et al., 1997, International Journal of Cancer 72:942–948; Kosaki et al., 1999, Cancer Research, 59: 1141–1145; Turley, 1992, Cancer and Metastasis Reviews 11:21–30; Tzanakakis et al., 1997 Biochimie. 79: 323–332; Zetter, 1993, Seminars in Cancer Biology 4: 219–229). Additionally, tumor cells can alter their interactions with ECM molecules by changing the composition of their cellular receptors, for example, the upregulation of the HA binding molecules RHAMM and CD44 (Goldbrunner et al., 1999, Acta Neurochirurgica 141: 295–305; Hall and Turley, 1995, Journal of Neuro-Oncology 26: 221–229; Hall et al., 1995, Cell 82: 19–28; Merzak et al., 1994, Cancer Research 54: 3988–3992). Further, malignant cells can degrade the existing normal matrix by producing proteolytic enzymes to digest the surrounding ECM (Furcht et al., 1994, Laboratory Investigation 70: 781–783; Mignatti and Rifkin, 1993, Physiological Reviews 73: 161–195; Stetler-Stevenson et al., 1993, FASEB Journal 7: 1434–1441). While the mechanisms that facilitate the invasion of tumor cells into adjacent tissue are diverse, it is perhaps the ability of malignant tumors to modify the composition of the surrounding matrix, including the production and digestion of matrix molecules, that best characterizes the invasive phenotype.

The role of proteases in the invasive process has been demonstrated in tumors of almost every tissue type (Furcht et al., 1994, Laboratory Investigation 70: 781–783; Mignatti and Rifkin, 1993, Physiological Reviews 73: 161–195; Stetler-Stevenson et al., 1993, FASEB Journal 7: 1434–1441), and have been strongly implicated in the invasive properties of high grade gliomas (DeClerck et al., 1991, Cancer Research 51: 2151–2157; Mohanam et al., 1994, Journal of Neuro-Oncology 22: 153–160; Nakagawa et al., 1994, Journal of Neurosurgery 81: 69–77; Rao et al., 1993, Cancer Research 53: 2208–2211; Rao et al., 1994, Journal of Neuro-Oncology 18: 129–138; Vaithilingham et al., 1992, Journal of Neurosurgery 77: 595–600; Yamamoto et al., 1994, Journal of Neuro-Oncology 22: 139–151). A wealth of literature has demonstrated that matrix metalloproteinases (MMPs), especially MMP-2 and MMP-9, are highly upregulated in gliomas, and that inhibition of these proteases can decrease glioma invasiveness (Deryugina et al., 1997, Journal of Cell Science 110: 2473–2482; Forsyth et al., 1999, British Journal of Cancer 79: 1828–1835; Hamasuna et al., 1999, International Journal of Cancer 82: 274–281; Rao et al., 1996, Clinical and Experimental Metastasis 14: 12–18; Sawaya et al., 1996, Clinical and Experimental Metastasis 14: 35–42; Uhm et al., 1996, Clinical and Experimental Metastasis 14: 421–433; Nakagawa et al., 1994, Journal of Neurosurgery 81: 69–77; Rao et al., 1993, Cancer Research 53: 2208–2211; Rao et al., 1994, Journal of Neuro-Oncology 18: 129–138). However, clinical trials employing MMP inhibitors for the treatment of primary tumors have been disappointing due to serious and deleterious side effects (Heath and Grochow, 2000, Drugs 59: 1043–1055).

One of the brain ECM molecules that plays an important role in glioma invasiveness and tumor progression is brain-enriched hyaluronan binding (BEHAB) protein (Hockfield et al., 1997, U.S. Pat. No. 5,635,370). BEHAB is a member of the proteoglycan tandem-repeat family of proteins, and exists as a both a secreted and GPI-anchored protein with a hyaluronan binding domain (Jaworski et al., 1994, J. Cell Biol. 125: 495–509; Yamada et al., 1994, J. Biol. Chem 269:10119–10126; Seidenbecher et al., 1995, J. Biol. Chem. 270: 27206–27212). Recent studies have demonstrated that BEHAB is a brain specific protein that is down-regulated as development progresses in the human brain (Gary et al., 2000, Gene 256: 139–147). Importantly, BEHAB is upregulated about 700% in almost all adult human glioma samples assayed to date (Jaworski et al., 1996, Cancer Research, 56: 2293–2298, Gary et al., 2000, Gene 256: 139–147).

BEHAB cleavage plays a prominent role in the progression of glioma. Recent work by Matthews et al. (2000, J. Biol. Chem. 275: 22695–22703) demonstrated that BEHAB is cleaved between $Glu^{395}$-$Ser^{396}$ into 50 kDa and 90 kDa fragments by a metalloproteinase, but not by an MMP. Instead, BEHAB is cleaved by a member of the a disintegrin and metalloproteinase with thrombospondin motifs (ADAMTS) family of metalloproteinases, specifically, ADAMTS4.

Unfortunately, due to deleterious side effects, traditional metalloproteinase inhibitors have proved to be an ineffective method for treating gliomas. Given the inherent risks of both diagnosing and treating gliomas with conventional techniques, and the failure of newer treatment regimens such as metalloproteinase inhibitors, there exists a long felt need for a method to both diagnose and treat primary central nervous system (CNS) tumors. The present invention meets this need.

BRIEF SUMMARY OF THE INVENTION

The invention includes an isolated nucleic acid encoding a mammalian mutant BEHAB molecule, or a fragment thereof. In one aspect, the isolated nucleic acid has 99.7% identity to the nucleic acid sequence set forth in SEQ ID NO:4. In another aspect, the isolated nucleic acid comprises the nucleic acid sequence set forth in SEQ ID NO:4.

In a further aspect, the invention includes an isolated nucleic acid encoding a mammalian mutant BEHAB molecule, wherein the amino acid sequence of the mammalian mutant BEHAB molecule comprises the amino acid sequence set forth in SEQ ID NO:3.

Also included in the invention is an isolated polypeptide comprising a mammalian mutant BEHAB molecule. In one aspect, the mammalian mutant BEHAB molecule has 99.6% identity the amino acid sequence set forth in SEQ ID NO:3.

In one embodiment, the isolated nucleic acid of the invention further comprises a nucleic acid encoding a tag polypeptide covalently linked thereto. Preferably, the tag polypeptide is selected from the group consisting of a myc tag polypeptide, a glutathione-S-transferase tag polypeptide, a green fluorescent protein tag polypeptide, a myc-pyruvate kinase tag polypeptide, a $His_6$ tag polypeptide, an influenza virus hemagglutinin tag polypeptide, a flag tag polypeptide, and a maltose binding protein tag polypeptide.

In another aspect, the isolated nucleic acid of the invention further comprises a nucleic acid specifying a promoter/regulatory sequence operably linked thereto.

In addition, the invention includes a vector comprising the isolated nucleic acid of the invention. In one embodiment, the vector further comprises a nucleic acid specifying a promoter/regulatory sequence operably linked thereto.

Also included is a recombinant cell comprising the isolated nucleic acid of the invention or comprising the vector of the invention.

The invention additionally includes an isolated nucleic acid complementary to an isolated nucleic acid encoding a mammalian BEHAB molecule, or a fragment thereof, the complementary nucleic acid being in an antisense orientation. In one aspect, the nucleic acid is complementary to the nucleic acid sequence set forth in SEQ ID NO:5. In one embodiment, there is provided a recombinant cell and a vector comprising a mammalian BEHAB molecule, or a fragment thereof, the complementary nucleic acid being in an antisense orientation.

The invention also includes a method for treating a primary CNS tumor in a mammal. The method comprises administering to a mammal an effective amount of a BEHAB cleavage inhibitor, thereby treating a primary CNS tumor in the mammal. In one aspect, the BEHAB cleavage inhibitor is selected from the group consisting of an antibody, a protein, a protease inhibitor, and a peptidomimetic. In one embodiment, the antibody specifically binds BEHAB, or a fragment thereof. In another embodiment, the protein comprises the amino acid sequence set forth in SEQ ID NO:3, or a fragment thereof.

In addition, there is included in the invention a method for treating a primary CNS tumor in a mammal. The method comprises administering to a mammal an effective amount of a BEHAB expression inhibitor, thereby treating a primary CNS tumor in the mammal. In one aspect, the BEHAB expression inhibitor is selected from the group consisting of a ribozyme and an antisense nucleic acid. In one embodiment, the antisense nucleic acid is complementary to an isolated nucleic acid encoding a BEHAB molecule, or a fragment thereof. In another embodiment, the ribozyme is complementary to an isolated nucleic acid encoding a BEHAB molecule, or a fragment thereof.

Further included is a method of treating a primary CNS tumor in a mammal. The method comprises administering to a mammal an effective amount of an inhibitor of the activity of BEHAB cleavage products, thereby treating a primary CNS tumor in a mammal. In one aspect, the inhibitor of the activity of BEHAB cleavage products is an antibody. In one embodiment, the antibody specifically binds a BEHAB cleavage product.

The invention additionally includes a method of diagnosing a primary CNS tumor in a mammal. The method comprises obtaining a biological sample from a first mammal, assessing the level of a BEHAB nucleic acid molecule in the biological sample, and comparing the level of a BEHAB nucleic acid molecule in the biological sample with the level of a BEHAB nucleic acid molecule in a biological sample obtained from a second otherwise identical mammal, wherein a higher level of a BEHAB nucleic acid molecule in the biological sample from the first mammal compared with the level of a BEHAB nucleic acid molecule in the biological sample from the second otherwise identical mammal is an indication that first the mammal is afflicted with a primary CNS tumor, thereby diagnosing a primary CNS tumor in a mammal.

In one aspect, the biological sample is selected from the group consisting of blood, neural tissue, cerebrospinal fluid, urine, saliva and brain tissue.

Further included is a method of assessing the effectiveness of a treatment for a primary CNS tumor in a mammal. The method comprises assessing the level of a BEHAB molecule in the mammal before, during, or after administration of a treatment for a primary CNS tumor to the mammal, wherein a higher or lower level of the BEHAB molecule in the mammal during or after administration of the treatment for a primary CNS tumor with the level of the BEHAB molecule in the mammal before administration of the treatment for a primary CNS tumor is an indication of the effectiveness of the treatment for a primary CNS tumor in the mammal, thereby assessing the effectiveness of the treatment for a primary CNS tumor in the mammal.

In one aspect, the treatment for a primary CNS tumor is selected from the group consisting of chemotherapy, radiation therapy, and surgery.

In addition, there is provided a method of identifying a compound that affects expression of a BEHAB molecule in a cell. The method comprises contacting a cell with a test compound and comparing the level of BEHAB molecule expression in the cell with the level of BEHAB molecule expression in an otherwise identical cell not contacted with the test compound, wherein a higher or lower level of BEHAB molecule expression in the cell contacted with the test compound compared with the level of BEHAB molecule expression in the otherwise identical cell not contacted with the test compound is an indication that the test compound affects expression of the BEHAB molecule in a cell, thereby identifying a compound that affects expression of the BEHAB molecule in a cell.

Also included is a compound identified by the aforementioned method.

The invention further provides a method of identifying a compound that reduces expression of a BEHAB molecule in a cell. The method comprises contacting a cell with a test compound and comparing the level of BEHAB molecule expression in the cell with the level of BEHAB molecule expression in an otherwise identical cell not contacted with the test compound, wherein a higher or lower level of BEHAB molecule expression in the cell contacted with the test compound compared with the level of BEHAB molecule expression in the otherwise identical cell not contacted with the test compound is an indication that the test compound reduces expression of the BEHAB molecule in a cell, thereby identifying a compound that reduces expression of the BEHAB molecule in a cell.

In addition, there is provided a compound identified by the aforementioned method.

The invention also includes a method of identifying a compound that inhibits BEHAB cleavage in a cell. The method comprises contacting a cell with a test compound and comparing the level of BEHAB cleavage in the cell with the level of BEHAB cleavage in an otherwise identical cell not contacted with the test compound, wherein a higher or lower level of BEHAB cleavage in the cell contacted with the test compound compared with the level of BEHAB cleavage in the otherwise identical cell not contacted with the test compound is an indication that the test compound inhibits BEHAB cleavage in a cell, thereby identifying a compound that inhibits BEHAB cleavage in a cell.

In addition, there is provided a method of identifying a compound that inhibits BEHAB cleavage in a cell-free system. The method comprises contacting the cell-free system with a test compound and comparing the level of BEHAB cleavage in the cell-free system with the level of BEHAB cleavage in an otherwise identical cell-free system not contacted with the test compound, wherein a higher or lower level of BEHAB cleavage in the cell-free system contacted with the test compound compared with the level of BEHAB cleavage in the otherwise identical cell-free system not contacted with the test compound is an indication that the test compound inhibits BEHAB cleavage in a cell-free system, thereby identifying a compound that inhibits BEHAB cleavage in a cell-free system.

Also included is a kit for treating a primary CNS tumor. The kit comprises a BEHAB cleavage inhibiting amount of a composition comprising an isolated nucleic acid molecule encoding a mutant BEHAB molecule, or a fragment thereof, and a pharmaceutically-acceptable carrier, the kit further comprising an applicator, and an instruction manual for the use thereof.

In addition, there is included a kit for treating a primary CNS tumor, wherein the kit comprises a BEHAB cleavage inhibiting amount of a composition comprising an isolated mutant BEHAB polypeptide, or a fragment thereof, and a pharmaceutically-acceptable carrier, the kit further comprising an applicator, and an instructional material for the use thereof.

Further, there is included a kit for treating a primary CNS tumor, wherein the kit comprises a BEHAB cleavage inhibiting amount of a composition comprising an antibody that specifically binds with a mammalian BEHAB molecule, or a fragment thereof, and a pharmaceutically acceptable carrier, the kit further comprising an applicator, and an instructional material for use thereof.

There is also provided a kit for treating a primary CNS tumor, wherein the kit comprises a BEHAB molecule expression inhibiting amount of a composition comprising an isolated nucleic acid complementary to an isolated nucleic acid encoding a mammalian BEHAB molecule, or some fragment thereof, the complementary nucleic acid being in an antisense orientation, and a pharmaceutically acceptable carrier, the kit further comprising an applicator, and an instructional material for the use thereof.

Another kit for treating a primary CNS tumor is also included. The kit comprises a BEHAB cleavage product inhibiting amount of a composition comprising an antibody that specifically binds with a BEHAB cleavage product, or a fragment thereof, and a pharmaceutically-acceptable carrier, the kit further comprising an applicator, and an instructional material for use thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIG. 1A depicts Western blots of media from cells transiently transfected with full-length (FL) and mutant (NVY) BEHAB. Both cell lines exhibit strong staining of the 145 kDa full-length protein. In contrast, no cleavage product was detected in the NVY mutant using the B50 antibody, while a 50 kDa cleavage product was detected in the media of cells transfected with the FL. FIG. 1B depicts Western blots of media from cells transiently co-transfected with 2 $\mu$g of the FL construct and 0, 1, 2, or 4 $\mu$g of the NVY mutant construct. Transfection of the NVY mutant increased the amount of full-length BEHAB, but had no effect on cleavage of normal BEHAB as seen using the B50 antibody. FIG. 1C depicts Western blots of media from cells stably transfected with full-length (FL) and mutant (NVY) BEHAB. Expression of BEHAB was examined in the CNS-1-FL and CNS-1-NVY cells using the B6 and B50 antibodies. As with the transient transfections, cells stably transfected with CNS-1-FL produced and cleaved BEHAB, whereas cells stably transfected with CNS-1-NVY produced the full-length protein but did not cleave it.

FIG. 2, comprising FIG. 2A is a graph depicting cell proliferation over seven days using the MTT assay. Data show changes in absorbance. Transfection using CNS-1-FL, CNS-1-GFP, and CNS-1-NVY had no effect on cell proliferation. FIG. 2B is a graph depicting cell death over seven days as evaluated using the LDH assay. Transfections using CNS-1-FL, CNS-1-GFP, and CNS-1-NVY had no effect on cell death.

FIG. 3, comprising FIG. 3A depicts an image of a representative tumor derived from CNS-1-GFP cells. FIG. 3B depicts an image of a representative tumor derived from CNS-1-FL cells. FIG.

3C depicts an image of a representative tumor derived from CNS-1-NVY cells. The CNS-1-FL tumor is larger and more invasive than the CNS-1-GFP and CNS-1-NVY tumors. FIG. 3D is a graph depicting volumes of tumors derived from CNS-1-FL, CNS-1-GFP, and CNS-1-NVY cells. These data were quantified by image analysis and volume reconstruction, and individual data points are represented by an asterisk.

DETAILED DESCRIPTION OF THE INVENTION

Figure 1A:
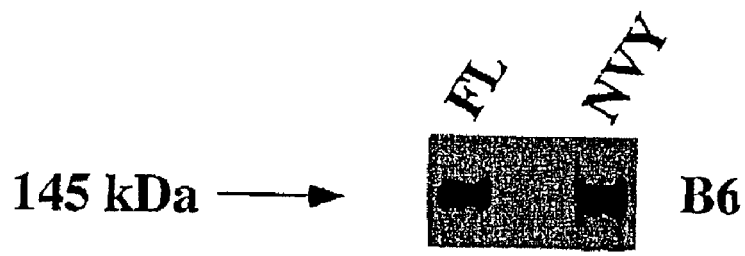
FIGS. 1A through 1C, depicts images of Western blot analysis of media from cells stably (FIG. 1C) or transiently (FIGS. 1A and 1B) transfected with full-length and/or mutant BEHAB.

Manipulation of the extracellular matrix (ECM) of the brain plays an important role in the progression and invasive phenotype of primary CNS tumors. One component of the ECM, brain-enriched hyaluronan binding (BEHAB) protein is vital in glioma cell motility, and thus invasiveness. The data disclosed herein demonstrate for the first time, that affecting BEHAB function and/or cleavage mediates a decrease in tumor size and an increase in survival time in animals with primary CNS tumors. Therefore, the present invention includes compositions and methods for the treatment of primary CNS tumors, including, but not limited to gliomas, oligodendroglioma, astrocytoma, gliosarcoma, glioblastoma multiforme, lymphoma, and reactive gliosis following brain injury.

The present invention also includes compositions and methods for diagnosing primary CNS tumors in a mammal. That is, the data disclosed herein demonstrate that a primary CNS tumor, including, but not limited to, gliomas, oligodendroglioma, astrocytoma, and gliosarcoma, may be diagnosed in a mammal using the methods disclosed herein.
Definitions As used herein, each of the following terms has the meaning associated with it in this section.

The articles "a" and "an" are used herein to refer to one or to more than one (i.e. to at least one) of the grammatical object of the article. By way of example, "an element" means one element or more than one element.

"Amplification" refers to any means by which a polynucleotide sequence is copied and thus expanded into a larger number of polynucleotide molecules, e.g., by reverse transcription, polymerase chain reaction, and ligase chain reaction.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879–5883; Bird et al., 1988, Science 242:423–426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

By the term "applicator" as the term is used herein, is meant any device including, but not limited to, a hypodermic syringe, a pipette, and the like, for administering the mutant BEHAB nucleic acid, protein, and/or anti-BEHAB antibodies and the antisense BEHAB nucleic acid of the invention to a mammal.

"BEHAB" "normal BEHAB", or "endogenous BEHAB" as the terms are used synonymously herein, refers to the Brain-Enriched Hyaluronan Binding molecule, otherwise known as brevican, present in its naturally-occurring state in a mammal.

"Biological sample," as that term is used herein, means a sample obtained from a mammal that can be used to assess the level of expression of a BEHAB, the level of BEHAB protein present, or both. Such a sample includes, but is not limited to, a blood sample, a neural tissue sample, a brain sample, and a cerebrospinal fluid sample.

"Cleavage" is used herein to refer to the disassociation of a peptide bond between two amino acids in a polypeptide, thereby separating the polypeptide comprising the two amino acids into at least two fragments.

A "cleavage inhibitor" is used herein to refer to a molecule, compound or composition that prevents the cleavage of a polypeptide either by titrating the protease responsible for cleavage, blocking the cleavage site, or otherwise making the cleavage site unrecognizable to a protease.

"Cleavage inhibiting amount" is used herein to refer to an effective amount of a cleavage inhibitor.

"Cleavage products" is used herein to refer to the fragments of an initial polypeptide resulting from the cleavage of the initial polypeptide into two or more fragments. As an example, the cleavage products of the 145 kDa BEHAB protein include 90 kDa and 50 kDa fragments.

By "complementary to a portion or all of the nucleic acid encoding BEHAB" is meant a sequence of nucleic acid which does not encode a BEHAB protein. Rather, the sequence which is being expressed in the cells is identical to the non-coding strand of the nucleic acid encoding a BEHAB protein and thus, does not encode BEHAB protein.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g. amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

A first region of an oligonucleotide "flanks" a second region of the oligonucleotide if the two regions are adjacent one another or if the two regions are separated by no more than about 1000 nucleotide residues, and preferably no more than about 100 nucleotide residues.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 500 nucleotides, even more preferably, at least about 500 nucleotides to about 1000 nucleotides, yet even more preferably, at least about 1000 to about 1500, even more preferably, at least about 1500 nucleotides to about 2000 nucleotides, yet even more preferably, at least about 2000 to about 2500, even more preferably, at least about 2500 nucleotides to about 2600 nucleotides, yet even more preferably, at least about 2600 to about 2650, and most preferably, the nucleic acid fragment will be greater than about 2652 nucleotides in length.

As applied to a protein, a "fragment" of BEHAB is about 20 amino acids in length. More preferably, the fragment of a BEHAB is about 100 amino acids, even more preferably, at least about 200, yet more preferably, at least about 300, even more preferably, at least about 400, yet more preferably, at least about 500, even more preferably, about 600, and more preferably, even more preferably, at least about 700, yet more preferably, at least about 800, even more preferably, about 850, and more preferably, at least about 884 amino acids in length.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequence.

"Mutant BEHAB" is used herein to refer to a Brain Enriched Hyaluronan Binding molecule in which the amino acid sequence has been modified to inhibit cleavage by proteases.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is naturally-occurring.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

"Primary CNS tumor" is used herein to refer to a neoplasia with origins in the brain, in that the cancerous cells did not originate in another part of the body and metastasize to the brain. Examples of primary CNS tumors include, but are not limited to, gliomas, well-differentiated astrocytomas, anaplastic astrocytomas, glioblastoma multiforme, ependymomas, oligodendrogliomas, ganglioneuromas, mixed gliomas, brain stem gliomas, optic nerve gliomas, meningiomas, pineal tumors, pituitary tumors, pituitary adenomas, reactive gliosis, primitive neuroectodermal tumors, schwannomas, lymphomas, vascular tumors, and lymphomas.

"Treating a primary CNS tumor" is used herein to refer to a situation where the severity of a symptom of a primary CNS tumor, including the volume of the tumor or the frequency with which any symptom or sign of the tumor is experienced by a patient, or both, is reduced, or where time to tumor progression or survival time is increased.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

By the term "specifically binds," as used herein, is meant an antibody which recognizes and binds an epitope of a BEHAB protein, but does not substantially recognize or bind other molecules in a sample.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

A "transgene", as used herein, means an exogenous nucleic acid sequence comprising a nucleic acid which encodes a promoter/regulatory sequence operably linked to nucleic acid which encodes an amino acid sequence, which exogenous nucleic acid is encoded by an animal or cell.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Description

I. Isolated Nucleic Acids

A. Sense Nucleic Acids

The present invention includes an isolated nucleic acid encoding a mammalian mutant BEHAB molecule, or a fragment thereof, wherein the nucleic acid shares at least about 99.7% identity with a nucleic acid having the sequence of SEQ ID NO:4. The mammal is preferably a human. Preferably, the nucleic acid is about 99.8% homologous, more preferably, and most preferably, about 99.9% homologous to SEQ ID NO:4, disclosed herein. Even more preferably, the nucleic acid is SEQ ID NO:4. The isolated nucleic acid of the invention should be construed to include an RNA or a DNA sequence encoding a mutant BEHAB protein of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

The present invention should not be construed as being limited solely to the nucleic and amino acid sequences disclosed herein. Once armed with the present invention, it is readily apparent to one skilled in the art that other nucleic acids encoding mutant BEHAB proteins can be obtained by following the procedures described herein in the experimental details section for the generation of other mammalian mutant BEHAB nucleic acids encoding mutant BEHAB polypeptides as disclosed herein (e.g., site-directed mutagenesis, frame shift mutations, and the like), and procedures that are well-known in the art or to be developed.

Further, any other number of procedures may be used for the generation of derivative or variant forms of mutant BEHAB using recombinant DNA methodology well known in the art such as, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York).

Procedures for the introduction of amino acid changes in a protein or polypeptide by altering the DNA sequence encoding the polypeptide are well known in the art and are also described in Sambrook et al. (1989, supra); Ausubel et al. (1997, supra).

The invention includes a nucleic acid encoding a mammalian mutant BEHAB wherein a nucleic acid encoding a tag polypeptide is covalently linked thereto. That is, the invention encompasses a chimeric nucleic acid wherein the nucleic acid sequence encoding a tag polypeptide is covalently linked to the nucleic acid encoding a mutant BEHAB polypeptide. Such tag polypeptides are well known in the art and include, for instance, green fluorescent protein (GFP), myc, myc-pyruvate kinase (myc-PK), $His_6$, maltose biding protein (MBP), an influenza virus hemagglutinin tag polypeptide, a flag tag polypeptide (FLAG), and a glutathione-S-transferase (GST) tag polypeptide. However, the invention should in no way be construed to be limited to the nucleic acids encoding the above-listed tag polypeptides. Rather, any nucleic acid sequence encoding a polypeptide which may function in a manner substantially similar to these tag polypeptides should be construed to be included in the present invention.

The nucleic acid comprising a nucleic acid encoding a tag polypeptide can be used to localize mutant BEHAB within a cell, a tissue, and/or a whole organism (e.g., a mammalian embryo), detect mutant BEHAB secreted from a cell, and to study the role(s) of mutant BEHAB in a cell. Further, addition of a tag polypeptide facilitates isolation and purification of the "tagged" protein such that the proteins of the invention can be produced and purified readily.

B. Antisense Nucleic Acids

In certain situations, it may be desirable to inhibit expression of BEHAB and the invention therefore includes compositions useful for inhibition of BEHAB expression. Thus, the invention features an isolated nucleic acid complementary to a portion or all of a nucleic acid encoding a mammalian BEHAB molecule which nucleic acid is in an antisense orientation with respect to transcription. Preferably, the antisense nucleic acid is complementary with a nucleic acid having at least about 99.7% homology with SEQ ID NO:5, or a fragment thereof. Preferably, the nucleic acid is about 99.8% homologous, and most preferably, about 99.9% homologous to a nucleic acid complementary to a portion or all of a nucleic acid encoding a mammalian BEHAB having the sequence of SEQ ID NO:5, or a fragment thereof, which is in an antisense orientation with respect to transcription. Most preferably, the nucleic acid is complementary to a portion or all of a nucleic acid that is SEQ ID NO:5, or a fragment thereof. Such antisense nucleic acid serves to inhibit the expression, function, or both, of a BEHAB molecule.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see Cohen, 1989, In: Oligodeoxyribonucleotides, Antisense Inhibitors of Gene Expression, CRC Press, Boca Raton, Fla.; Tullis, 1991, U.S. Pat. No. 5,023,243,) incorporated by reference herein in its entirety.

II. Isolated Polypeptides

The invention also includes an isolated polypeptide comprising a mammalian mutant BEHAB molecule. Preferably, the isolated polypeptide comprising a mammalian mutant BEHAB molecule is at least about 99.6% homologous to a polypeptide having the amino acid sequence of SEQ ID NO:3, or some fragment thereof. Preferably, the isolated polypeptide is about 99.7% homologous, more preferably, about 99.8% homologous, more preferably, and most preferably, about 99.9% homologous to SEQ ID NO:3, or some fragment thereof. Most preferably, the isolated polypeptide comprising a mutant BEHAB molecule is SEQ ID NO:3.

The present invention also provides for analogs of proteins or peptides which comprise a mutant BEHAB molecule as disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;

valine, isoleucine, leucine;

aspartic acid, glutamic acid;

asparagine, glutamine;

senne, threonine;

lysine, arginine;

phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "derivatives," and "variants" of the peptides of the invention (or of the DNA encoding the same) which derivatives and variants are mutant BEHAB peptides which are altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein, in that the peptide has biological/biochemical properties of the mutant BEHAB peptide of the present invention.

A biological property of a mutant BEHAB protein should be construed to but not be limited to include the ability of the peptide to be secreted from a cell, or anchored via a GPI-linkage, the ability to not be cleaved by a protease, and the like.

The skilled artisan would understand, based upon the disclosure provided herein, that mutant BEHAB biological activity encompasses, but is not limited to, the ability of a molecule or compound to be expressed in brain tissue, to be detected in brain tissue, to be secreted from a cell, to be anchored to a cell, to not be cleaved by a protease, and the like. "Mutant BEHAB activity" includes the effects of mutant BEHAB, either that circulating in the ECM or cerebrospinal fluid or that produced locally in the brain. Mutant BEHAB biological activity mediates, is associated with, or both, inter alia, tumor progression, tumor invasiveness, tumor volume and size, animal survival, and the like.

III. Vectors

In other related aspects, the invention includes an isolated nucleic acid encoding a mammalian mutant BEHAB operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

Expression of mutant BEHAB, either alone or fused to a detectable tag polypeptide, in cells which either normally express normal BEHAB, may be accomplished by generating a plasmid, viral, or other type of vector comprising the desired nucleic acid operably linked to a promoter/regulatory sequence which serves to drive expression of the protein, with or without tag, in cells in which the vector is introduced. Many promoter/regulatory sequences useful for driving constitutive expression of a gene are available in the art and include, but are not limited to, for example, the cytomegalovirus immediate early promoter enhancer sequence, the SV40 early promoter, both of which were used in the experiments disclosed herein, as well as the Rous sarcoma virus promoter, and the like. Moreover, inducible and tissue specific expression of the nucleic acid encoding mutant BEHAB may be accomplished by placing the nucleic acid encoding mutant BEHAB, with or without a tag, under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention includes the use of any promoter/regulatory sequence, which is either known or unknown, and which is capable of driving expression of the desired protein operably linked thereto.

Expressing mutant BEHAB using a vector allows the isolation of large amounts of recombinantly produced protein. Further, where the expression of normal BEHAB expression causes a disease, disorder, or condition associated with such expression, the expression of mutant BEHAB driven by a promoter/regulatory sequence can provide useful therapeutics including, but not limited to, gene therapy whereby mutant BEHAB is provided. A disease, disorder or condition associated with an increased level of expression, level of protein, or increased level of cleavage and/or activity of the protein or its cleavage products, for which administration of mutant BEHAB can be useful can include, but is not limited to, primary CNS tumors, gliomas, well-differentiated astrocytomas, anaplastic astrocytomas, glioblastoma multiforme, ependymomas, oligodendrogliomas, ganglioneuromas, mixed gliomas, brain stem gliomas, optic nerve gliomas, meningiomas, pineal tumors, pituitary tumors, pituitary adenomas, primitive neuroectodermal tumors, schwannomas, vascular tumors, lymphomas and the like.

Therefore, the invention includes not only methods of inhibiting normal BEHAB expression, translation, cleavage and/or activity, but it also includes methods relating to decreasing BEHAB expression, protein level, cleavage and/or activity since decreasing BEHAB expression, cleavage and/or activity or increasing mutant BEHAB expression and/or activity can be useful in providing effective therapeutics.

Selection of any particular plasmid vector or other DNA vector is not a limiting factor in this invention and a wide plethora of vectors are well-known in the art. Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

The invention thus includes a vector comprising an isolated nucleic acid encoding a mammalian mutant BEHAB. The incorporation of a desired nucleic acid into a vector and the choice of vectors is well-known in the art as described in, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

The invention also includes cells, viruses, proviruses, and the like, containing such vectors. Methods for producing cells comprising vectors and/or exogenous nucleic acids are well-known in the art. See, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

The nucleic acids encoding mutant BEHAB may be cloned into various plasmid vectors. However, the present invention should not be construed to be limited to plasmids or to any particular vector. Instead, the present invention should be construed to encompass a wide plethora of vectors which are readily available and/or well-known in the art.

IV. Recombinant Cells

The invention includes a recombinant cell comprising, inter alia, an isolated nucleic acid encoding mutant BEHAB, an antisense nucleic acid complementary thereto, a nucleic acid encoding an antibody that specifically binds BEHAB or its cleavage products, and the like. In one aspect, the recombinant cell can be transiently transfected with a plasmid encoding a portion of the nucleic acid encoding mutant BEHAB. The nucleic acid need not be integrated into the cell genome nor does it need to be expressed in the cell. Moreover, the cell may be a prokaryotic or a eukaryotic cell and the invention should not be construed to be limited to any particular cell line or cell type. Such cells include, but are not limited to, neurons, neural cells, brain cells, glioma-derived cell lines, glial cell lines, non-glial cell lines, stem cell lines, and the like.

Further, it is important to note that the purpose of transgene-comprising, i.e., recombinant, cells should not be construed to be limited to the generation of intracranial tumors. Rather, the invention should be construed to include any cell type into which a nucleic acid encoding a mammalian mutant BEHAB is introduced, including, without limitation, a prokaryotic cell and a eukaryotic cell comprising an isolated nucleic acid encoding mammalian mutant BEHAB.

The invention includes a eukaryotic cell which, when the transgene of the invention is introduced therein, and the protein encoded by the desired gene is expressed therefrom, where it was not previously present or expressed in the cell or where it is now expressed at a level or under circumstances different than that before the transgene was introduced, a benefit is obtained. Such a benefit may include the fact that there has been provided a system wherein the expression of the desired gene can be studied in vitro in the laboratory or in a mammal in which the cell resides, a system wherein cells comprising the introduced gene can be used as research, diagnostic and therapeutic tools, and a system wherein mammal models are generated which are useful for the development of new diagnostic and therapeutic tools for selected disease states in a mammal.

A cell expressing an isolated nucleic acid encoding mutant BEHAB can be used to provide mutant BEHAB to a cell, tissue, or whole mammal where a higher level of mutant BEHAB can be useful to treat or alleviate a disease, disorder or condition associated with normal BEHAB expression, cleavage, and/or activity. Such diseases, disorders or conditions can include, but are not limited to, primary CNS tumors, gliomas, well-differentiated astrocytomas, anaplastic astrocytomas, glioblastoma multiforme, ependymomas, oligodendrogliomas, ganglioneuromas, mixed gliomas, brain stem gliomas, optic nerve gliomas, meningiomas, pineal tumors, pituitary tumors, pituitary adenomas, primitive neuroectodermal tumors, schwannomas, vascular tumors, lymphomas, and the like. Therefore, the invention includes a cell expressing mutant BEHAB to decrease or prevent normal BEHAB expression, translation, cleavage and/or activity, where increasing mutant BEHAB expression, protein level, and/or activity can be useful to treat or alleviate a disease, disorder or condition.

One of ordinary skill would appreciate, based upon the disclosure provided herein, that a "knock-in" or "knock-out" vector of the invention comprises at least two sequences homologous to two portions of the nucleic acid which is to be replaced or deleted, respectively. The two sequences are homologous with sequences that flank the gene; that is, one sequence is homologous with a region at or near the 5' portion of the coding sequence of the nucleic acid encoding normal BEHAB and the other sequence is further downstream from the first. One skilled in the art would appreciate, based upon the disclosure provided herein, that the present invention is not limited to any specific flanking nucleic acid sequences. Instead, the targeting vector may comprise two sequences which remove some or all of, for example, normal BEHAB (i.e., a "knock-out" vector) or which insert (i.e., a "knock-in" vector) a nucleic acid encoding mutant BEHAB, or a fragment thereof, from or into a mammalian genome, respectively. The crucial feature of the targeting vector is that it comprise sufficient portions of two sequences located towards opposite, i.e., 5' and 3', ends of the normal BEHAB open reading frame (ORF) in the case of a "knock-out" vector, to allow deletion/insertion by homologous recombination to occur such that all or a portion of the nucleic acid encoding normal BEHAB is deleted from a location on a mammalian chromosome.

The design of transgenes and knock-in and knock-out targeting vectors is well-known in the art and is described in standard treatises such as Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York), and the like. The upstream and downstream portions flanking or within the BEHAB coding region to be used in the targeting vector may be easily selected based upon known methods and following the teachings disclosed herein based on the disclosure provided herein including the nucleic and amino acid sequences of mammalian BEHAB and mutant BEHAB. Armed with these sequences, one of ordinary skill in the art would be able to construct the transgenes and knock-out vectors of the invention.

One skilled in the art would appreciate, based upon this disclosure, that cells comprising decreased levels of normal BEHAB protein, decreased levels of BEHAB and/or BEHAB cleavage product activity, or both, include, but are not limited to, cells expressing inhibitors of BEHAB expression (e.g., antisense or ribozyme molecules, synthetic antibodies or intrabodies).

Methods and compositions useful for maintaining mammalian cells in culture are well known in the art, wherein the mammalian cells are obtained from a mammal including, but not limited to, cells obtained from a mouse, a rat, a human, and the like.

The recombinant cell of the invention can be used to study the effect of qualitative and quantitative alterations in BEHAB levels on tumor progression and invasiveness. This is because the fact that BEHAB is secreted and possesses a hyaluronan binding domain indicates that BEHAB is involved in the function, composition, or activity of the ECM. Further, the recombinant cell can be used to produce mutant BEHAB for use for therapeutic and/or diagnostic purposes. That is, a recombinant cell expressing mutant BEHAB can be used to produce large amounts of purified and isolated mutant BEHAB that can be administered to treat or alleviate a disease, disorder or condition associated with or caused by BEHAB expression, activity, and/or cleavage.

Alternatively, recombinant cells expressing mutant BEHAB can be administered in ex vivo and in vivo therapies where administering the recombinant cells thereby administers the protein to a cell, a tissue, and/or a mammal. Additionally, the recombinant cells are useful for the discovery of BEHAB receptor and BEHAB signaling pathways.

The recombinant cell of the invention, wherein the cell has been engineered such that it does not express BEHAB, or expresses mutant BEHAB lacking cleavability, can also be used in ex vivo and in vivo cell therapies where either a mammal's own cells (e.g., neural cells, brain cells, and the like) or those of a syngeneic matched donor are recombinantly engineered as described elsewhere herein (e.g., by insertion of an antisense nucleic acid or a knock-out vector such that BEHAB expression and/or protein levels are thereby reduced in the recombinant cell), and the recombinant cell is administered to the recipient mammal. In this way, recombinant cells that express BEHAB at a reduced level can be administered to a mammal whose own cells express increased levels of BEHAB thereby treating or alleviating a disease, disorder or condition associated with or mediated by increased BEHAB expression as disclosed elsewhere herein.

V. Antibodies

Also included is an antibody that specifically binds BEHAB, a BEHAB cleavage product, or fragments thereof. One skilled in the art would understand, based upon the disclosure provided herein, that an antibody that specifically binds BEHAB and/or a BEHAB cleavage product, binds with a BEHAB protein, or an immunogenic portion thereof, preferably the cleavage site discussed elsewhere herein. In one embodiment, the antibody is directed to mammalian BEHAB comprising the amino acid sequence SEQ ID NO:6.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.). Such techniques include immunizing an animal with a chimeric protein comprising a portion of another protein such as a maltose binding protein or glutathione (GSH) tag polypeptide portion, and/or a moiety such that the BEHAB portion is rendered immunogenic (e.g., BEHAB conjugated with keyhole limpet hemocyanin, KLH) and a portion comprising the respective rodent and/or human BEHAB amino acid residues. The chimeric proteins are produced by cloning the appropriate nucleic acids encoding BEHAB (e.g., SEQ ID NO:5 into a plasmid vector suitable for this purpose, such as but not limited to, pMAL-2 or pCMX. Other methods of producing antibodies that specifically bind BEHAB and portions thereof are detailed in Matthews et al. (2000, J. Biol. Chem. 275: 22695–22703).

However, the invention should not be construed as being limited solely to polyclonal antibodies that bind a full-length BEHAB. Rather, the invention should be construed to include other antibodies, as that term is defined elsewhere herein, to mammalian BEHAB, or portions thereof. Further, the present invention should be construed to encompass antibodies that, among other things, bind to BEHAB and are able to bind BEHAB present on Western blots, in immunohistochemical staining of tissues thereby localizing BEHAB in the tissues, and in immunofluorescence microscopy of a cell transiently or stably transfected with a nucleic acid encoding at least a portion of BEHAB.

One skilled in the art would appreciate, based upon the disclosure provided herein, that the antibody can specifically bind with any portion of the protein and the full-length protein can be used to generate antibodies specific therefor. However, the present invention is not limited to using the full-length protein as an immunogen. Rather, the present invention includes using an immunogenic portion of the protein to produce an antibody that specifically binds with mammalian BEHAB. That is, the invention includes immunizing an animal using an immunogenic portion, or antigenic determinant, of the BEHAB protein, for example, the epitope comprising the cleavage site, or a new antigenic site produced by proteolytic cleavage.

The antibodies can be produced by immunizing an animal such as, but not limited to, a rabbit or a mouse, with a BEHAB protein, or a portion thereof, or by immunizing an animal using a protein comprising at least a portion of BEHAB, or a fusion protein including a tag polypeptide portion comprising, for example, a maltose binding protein tag polypeptide portion, covalently linked with a portion comprising the appropriate BEHAB amino acid residues. One skilled in the art would appreciate, based upon the disclosure provided herein, that smaller fragments of these proteins can also be used to produce antibodies that specifically bind BEHAB.

One skilled in the art would appreciate, based upon the disclosure provided herein, that various portions of an isolated BEHAB polypeptide can be used to generate antibodies to either epitopes comprising the cleavage site of BEHAB or to epitopes present on the cleavage products of BEHAB. Once armed with the sequence of BEHAB and the detailed analysis localizing the various epitopes and cleavage products of the protein, the skilled artisan would understand, based upon the disclosure provided herein, how to obtain antibodies specific for the various portions of a mammalian BEHAB polypeptide using methods well-known in the art or to be developed.

Therefore, the skilled artisan would appreciate, based upon the disclosure provided herein, that the present invention encompasses antibodies that neutralize and/or inhibit BEHAB activity (e.g., by inhibiting necessary BEHAB cleavage product receptor/ligand interactions or BEHAB cleavage) which antibodies can recognize BEHAB or BEHAB cleavage products.

The invention should not be construed as being limited solely to the antibodies disclosed herein or to any particular immunogenic portion of the proteins of the invention. Rather, the invention should be construed to include other antibodies, as that term is defined elsewhere herein, to BEHAB, or portions thereof, or to proteins sharing at least about % homology with a polypeptide having the amino acid sequence of SEQ ID NO:6. Preferably, the polypeptide is about 1% homologous, more preferably, about 5% homologous, more preferably, about 10% homologous, even more preferably, about 20% homologous, more preferably, about 30% homologous, preferably, about 40% homologous, more preferably, about 50% homologous, even more preferably, about 60% homologous, more preferably, about 70% homologous, even more preferably, about 80% homologous, preferably, about 90% homologous, more preferably, about 95% homologous, even more preferably, about 99% homologous, and most preferably, about 99.9% homologous to BEHAB (SEQ ID NO:6).

One skilled in the art would appreciate, based upon the disclosure provided herein, that the antibodies can be used to localize the relevant protein in a cell and to study the role(s) of the antigen recognized thereby in cell processes. Moreover, the antibodies can be used to detect and or measure the amount of protein present in a biological sample using well-known methods such as, but not limited to, Western blotting and enzyme-linked immunosorbent assay (ELISA). Moreover, the antibodies can be used to immunoprecipitate and/or immuno-affinity purify their cognate antigen using methods well-known in the art. In addition, the antibody can be used to decrease the level of BEHAB or BEHAB cleavage products in a cell thereby inhibiting the effect(s) of BEHAB or BEHAB cleavage products in a cell. Thus, by administering the antibody to a cell or to the tissues of a mammal or to the mammal itself, the required BEHAB receptor/ligand interactions are therefore inhibited such that the effect of BEHAB cleavage is also inhibited. One skilled in the art would understand that inhibiting BEHAB cleavage using an anti-BEHAB antibody can include, but is not limited to, decreased tumor size, increased survival, and the like. One skilled in the art would appreciate, based upon the disclosure provided herein, that the invention encompasses administering an antibody that specifically binds with BEHAB orally, parenterally, intraventricularly, intrathecally, intraparenchymally or by multiple routes, to inhibit BEHAB cleavage in the brain. Administration can include delivery by bioengineered polymers, direct injection, through an Ommaya reservoir (A device implanted under the scalp that is used to deliver anticancer drugs to the cerebrospinal fluid, or other such means well known to one of skill in the art of neurosurgery.

The invention encompasses polyclonal, monoclonal, synthetic antibodies, and the like. One skilled in the art would understand, based upon the disclosure provided herein, that the crucial feature of the antibody of the invention is that the antibody bind specifically with BEHAB. That is, the antibody of the invention recognizes BEHAB, or a fragment thereof (e.g., an immunogenic portion or antigenic determinant thereof), on Western blots, in immunostaining of cells, and immunoprecipitates BEHAB using standard methods well-known in the art.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109–115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125–168), and the references cited therein. Further, the antibody of the invention may be "humanized" using the technology described in, for example, Wright et al. (1992, Critical Rev. Immunol. 12:125–168), and in the references cited therein, and in Gu et al. (1997, Thrombosis and Hematocyst 77:755–759). The present invention also includes the use of humanized antibodies specifically reactive with epitopes of BEHAB. Such antibodies are capable of specifically binding BEHAB, or a fragment thereof. The humanized antibodies of the invention have a human framework and have one or more complementarity determining regions (CDRs) from an antibody, typically, but not limited to a mouse antibody, specifically reactive with BEHAB, or a fragment thereof. Thus, for example, humanized antibodies to BEHAB are useful in the treatment of primary CNS tumors such as gliomas, well-differentiated astrocytomas, anaplastic astrocytomas, glioblastoma multiforme, ependymomas, oligodendrogliomas, ganglioneuromas, mixed gliomas, brain stem gliomas, optic nerve gliomas, meningiomas, pineal tumors, pituitary tumors, pituitary adenomas, primitive neuroectodermal tumors, schwannomas, vascular tumors, lymphomas, and the like.

When the antibody used in the invention is humanized, the antibody may be generated as described in Queen, et al. (U.S. Pat. No. 6,180,370), Wright et al., (1992, Critical Rev. Immunol. 12:125–168) and in the references cited therein, or in Gu et al. (1997, Thrombosis and Hematocyst 77(4): 755–759). The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as BEHAB, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

Human constant region (CDR) DNA sequences from a variety of human cells can be isolated in accordance with well known procedures. Preferably, the human constant region DNA sequences are isolated from immortalized B-cells as described in WO87/02671, which is herein incorporated by reference. CDRs useful in producing the antibodies of the present invention may be similarly derived from DNA encoding monoclonal antibodies capable of binding to BEHAB. Such humanized antibodies may be generated using well known methods in any convenient mammalian source capable of producing antibodies, including, but not limited to, mice, rats, rabbits, or other vertebrates. Suitable cells for constant region and framework DNA sequences and host cells in which the antibodies are expressed and secreted, can be obtained from a number of sources, for example, American Type Culture Collection, Manassas, Va.

In addition to the humanized antibodies discussed above, other modifications to native antibody sequences can be readily designed and manufactured utilizing various recombinant DNA techniques well known to those skilled in the art. Moreover, a variety of different human framework regions may be used singly or in combination as a basis for humanizing antibodies directed to BEHAB. In general, modifications of genes may be readily accomplished using a variety of well-known techniques, such as site-directed mutagenesis (Gillman and Smith, Gene, 8:81–97 (1979); Roberts et al., 1987, Nature, 328:731–734).

Alternatively, a phage antibody library may be generated. To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor Laboratory, New York).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al. (992, Critical Rev. Immunol. 12:125–168).

Processes such as those described above, have been developed for the production of human antibodies using M13 bacteriophage display (Burton et al., 1994, Adv. Immunol. 57:191–280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222:581–597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837–839; de Kruif et al. 1995, J. Mol. Biol. 248:97–105).

VI. Methods

A. Methods of Treating a Primary CNS Tumor

The present invention is based, in part, on the novel discovery that BEHAB plays a significant role in primary CNS tumor progression, invasiveness and the survival time of mammals with brain tumors. As demonstrated by the data disclosed herein, BEHAB cleavage potentiates the progression of primary CNS tumors, and inhibition of cleavage, and/or inhibition of the function of BEHAB and its cleavage products can be used as a treatment for a primary CNS tumor in a mammal. In all instances, whether treating or diagnosing a primary CNS tumor, the most preferred mammal is a human.

The present invention includes a method of treating a primary CNS tumor in a mammal, preferably a human. This is because, as demonstrated by the data disclosed elsewhere herein, cleavage of BEHAB, and/or the function, biological activity and expression of BEHAB cleavage products is critical to the progression and invasiveness of primary CNS tumors. Therefore, as is evident from the data presented herein, inhibiting the cleavage of BEHAB, and/or inhibiting the function, biological activity, and expression of BEHAB cleavage products can serve as a treatment for primary CNS tumors. One skilled in the art would appreciate, based on the present disclosure, that inhibiting the cleavage of BEHAB provides an important and novel therapeutic for the treatment of among other things, gliomas, well-differentiated astrocytomas, anaplastic astrocytomas, glioblastoma multiforme, ependymomas, oligodendrogliomas, ganglioneuromas, mixed gliomas, brain stem gliomas, optic nerve gliomas, meningiomas, pineal tumors, pituitary tumors, pituitary adenomas, primitive neuroectodermal tumors, schwannomas, vascular tumors, lymphomas, reactive gliosis, and the like. One of skill in the art will also recognize that primary CNS tumors arise from injury to the CNS, i.e. the brain and spinal cord. Such tumors that result from these injuries are well known in the art and often referred to as reactive gliosis. Reactive gliosis is detailed in, for example, Streit (2000, Toxicol. Pathol., 28:28–30). The present invention includes methods for treating reactive gliosis in a mammal, preferably a human.

An inhibitor of BEHAB cleavage is administered to a mammal, thereby decreasing BEHAB cleavage and providing a therapeutic benefit. The skilled artisan would appreciate, based upon the disclosure provided herein, that BEHAB cleavage can be inhibited using a wide range of techniques known or to be developed in the future. That is, the invention encompasses inhibiting the cleavage of BEHAB in a mammal, and thereby preventing the progression and invasiveness of a primary CNS tumor. The present invention discloses methods for inhibiting BEHAB cleavage in a mammal, e.g. blocking the cleavage site, titrating the protease responsible for cleavage, and expressing or administering a non-cleavable BEHAB mutant. This is because, as demonstrated by the data disclosed herein, affecting the cleavage of BEHAB mediates a variety of effects, including, but not limited to decreased tumor size and increased survival time in mammals afflicted with primary CNS tumors, and thereby provides a novel and powerful therapeutic for primary CNS tumors.

The skilled artisan will further understand when equipped with this disclosure and the data presented herein, that administering to a mammal an inhibitor of the function, biological activity, and expression of BEHAB and/or its cleavage products provides a beneficial therapeutic to a mammal with a primary CNS tumor. The present invention includes methods for reducing or preventing the expression of BEHAB and binding the cleavage products and/or their ligands. As demonstrated by the data disclosed herein, increased levels of BEHAB and the biological activity of BEHAB cleavage products mediate enhanced progression of primary CNS tumors, resulting in decreased survival rates and larger tumors. Therefore, a method for inhibiting BEHAB expression or BEHAB cleavage product expression and/or function is included in the present invention.

The skilled artisan would understand that inhibiting BEHAB cleavage encompasses blocking the cleavage site, titrating the protease responsible for cleavage, and expressing and/or administering a non-cleavable BEHAB mutant. The present invention includes a method for inhibiting the cleavage of BEHAB by blocking the cleavage site on the protein. As disclosed herein, the cleavage site comprises $Glu^{395}$-$Ser^{396}$ of the BEHAB protein. Therefore, inaccessibility of this cleavage site to a protease can prevent the cleavage of BEHAB. The present invention therefore includes methods for inhibiting the cleavage of BEHAB by blocking access to the cleavage site by proteases. As an example, an antibody to a portion of the protein comprising the cleavage site, or a peptide or a small molecule that interacts with the cleavage site, would block access to the protein by a protease, thereby inhibiting BEHAB cleavage. The skilled artisan would appreciate, when armed with the disclosure and data disclosed herein, that an antibody can specifically bind a short peptide comprising the cleavage site, or to a larger portion of the BEHAB protein, provided that the antibody blocks the cleavage site.

Methods of generating antibodies to BEHAB are well known in the art (Matthews et al., 2000, J. Biol. Chem. 275: 22695–22703) and are disclosed elsewhere herein. Further, methods for producing antibodies that specifically bind certain epitopes of a protein are well known in the art and can be accomplished using standard methods disclosed herein and elsewhere, see Harlow et al. (1988, Antibodies: A Laboratory Manual, Cold Spring Harbor, N.Y.).

One of skill in the art will appreciate that an antibody can be administered as a protein, a nucleic acid construct encoding a protein, or both. Numerous vectors and other compositions and methods disclosed elsewhere herein are well known for administering a protein or a nucleic acid construct encoding a protein to cells or tissues. Therefore, the invention includes a method of administering an antibody or a nucleic acid encoding an antibody (synthetic antibody) that is specific for BEHAB (Sambrook et al., 1989, Molecular Cloning: A Laboratory Manual, Cold Spring Harbor Laboratory, New York; Ausubel et al., 1997, Current Protocols in Molecular Biology, John Wiley & Sons, New York).

One skilled in the art would understand, based upon the disclosure provided herein, that an antibody can be administered such that it blocks the cleavage site on BEHAB present in a mammal. Moreover, the invention encompasses administering an antibody that specifically binds with BEHAB, or a nucleic acid encoding the antibody, wherein the molecule further comprises an intracellular retention sequence such that the antibody binds with BEHAB and prevents its GPI-anchored expression or secretion. Such antibodies, frequently referred to as "intrabodies", are well known in the art and are described in, for example, Marasco et al. (U.S. Pat. No. 6,004,490) and Beerli et al. (1996, Breast Cancer Research and Treatment 38:11–17). Thus, the invention encompasses methods comprising inhibiting BEHAB cleavage where BEHAB is present in a mammal, as well as methods of inhibiting BEHAB cleavage comprising inhibiting BEHAB being present in its GPI-anchored on a cell membrane form or its secreted, and such methods as become known in the future.

The present invention also encompasses methods for inhibiting BEHAB cleavage by inhibiting the protease responsible for BEHAB cleavage. This is because, as is evident from the data presented herein, BEHAB is cleaved by a protease at a specific site, but inhibiting the cleavage of BEHAB results in, among other things, smaller tumor volumes and increased animal survival rates. Therefore, the present invention includes a method of inhibiting BEHAB cleavage by inhibiting the protease that cleaves BEHAB.

One of skill in the art will recognize that inhibiting a protease comprises administering to a mammal an effective amount of a protease inhibitor. Such inhibitors include, but are not limited to, chemical compounds, including tissue inhibitor of metalloproteinases 2, tissue inhibitor of metalloproteinases 3, small molecules, an antibody that specifically binds a protease that cleaves BEHAB, and the like. Specific protease inhibitors are well known in the art, and are discussed in, for example, Martel-Pelletier et al., (2001, Best Pract. Res. Clin. Rheumatol. 15:805–29). The skilled artisan, when armed with the present disclosure and teachings herein, will readily understand how to administer a protease inhibitor to a mammal, and therefore, the present invention encompasses protease inhibitors as a treatment for primary CNS tumors.

The present invention also encompasses methods for inhibiting BEHAB cleavage by titrating the protease responsible for BEHAB cleavage. This is because, as is evident from the data presented herein, BEHAB is cleaved by a protease at a specific site, but the mutant BEHAB of the present invention cannot be cleaved by a protease, as measured in both in vivo and in vitro assays. Further, the protease that cleaves BEHAB is present in the body in limited amounts and limited locations compared to other metalloproteinases. Therefore, an uncleavable BEHAB is capable of titrating the protease so it is not available to cleave endogenous BEHAB. One of skill in the art will recognize that titrating a protease encompasses providing a substrate that reduces the functional concentration of the protease in a mammal, preferably a human, that is available to cleave BEHAB. Titrating a protease further includes providing a substrate that is recognized and bound by a protease, resulting in a decline in the number of proteases or protease active sites available to cleave BEHAB.

As described more fully elsewhere herein, a tumor expressing a mutant, uncleavable form of BEHAB, even in the presence of endogenous BEHAB, results in among other things, smaller tumor volumes and increase survival rates in animals. These data indicate that even though endogenous BEHAB is present in a cell, the additional presence of an uncleavable BEHAB results in the decreased progression of a primary CNS tumor in an art accepted in vivo primary CNS tumor model. The data further indicate that when tumors expressing exogenous mutant BEHAB are compared to tumors expressing exogenous normal BEHAB, tumors expressing mutant BEHAB are both smaller and result in longer animal survival times. While not wishing to be bound by any particular theory, the data presented herein indicate that an uncleavable BEHAB mutant titrates the protease responsible for BEHAB cleavage, and as a result of decreased cleavage, decreased tumor progression ensues.

The skilled artisan would appreciate, based on the present disclosure and the data disclosed herein that a non-cleavable substrate for the protease inhibits tumor progression by decreasing tumor size and increasing survival rates in animals afflicted with primary CNS tumors. Therefore, the present invention includes a method for treating a primary CNS tumor by titrating the protease that cleaves BEHAB.

Compounds used to titrate the protease that cleaves BEHAB include, but are not limited to, peptides, proteins, mimetopes and peptidomimetics. As disclosed elsewhere herein, non-cleavable BEHAB (mutant BEHAB, SEQ ID NO:3) comprises the native BEHAB protein with a mutation in the amino acid sequence surrounding the cleavage site, specifically a mutation of Glu-Ser-Glu-Ser-Arg-Gly to Glu-Ser-Glu-Asn-Val-Tyr (SEQ ID NO:1 and SEQ ID NO:2, respectively). One of skill in the art will readily appreciate that a peptide derived from full length mutant BEHAB can exhibit the same protease titrating properties as the full length mutant BEHAB protein set forth in SEQ ID NO:3. Thereby the present invention encompasses the full length mutant BEHAB protein and truncated mutant BEHAB peptides comprising protease titrating activity.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The peptides of the present invention may be readily prepared by standard, well-established solid-phase peptide synthesis (SPPS) as described by Stewart et al. (Solid Phase Peptide Synthesis, 2nd Edition, 1984, Pierce Chemical Company, Rockford, Ill.) and as described by Bodanszky and Bodanszky (The Practice of Peptide Synthesis, 1984, Springer-Verlag, New York). At the outset, a suitably protected amino acid residue is attached through its carboxyl group to a derivatized, insoluble polymeric support, such as cross-linked polystyrene or polyamide resin. "Suitably protected" refers to the presence of protecting groups on both the a-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxcarbonyl as the a-amino protecting group, and the FMOC method which utilizes 9-fluorenylmethyloxcarbonyl to protect the α-amino of the amino acid residues, both methods of which are well-known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF (hydrofluoric acid) treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequencers, which sequentially degrade the peptide and identify the amino acids in order, may also be used to determine definitely the sequence of the peptide.

Prior to its use, the peptide is purified to remove contaminants. In this regard, it will be appreciated that the peptide will be purified so as to meet the standards set out by the appropriate regulatory agencies or for specific uses. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

One of skill in the art would readily appreciate that a mutant BEHAB protein or peptide capable of titrating a protease that cleaves BEHAB may be administered to a mammal as an isolated nucleic acid encoding a mutant BEHAB protein or peptide. Methods of expressing a desired protein in a cell or a mammal are well known in the art, and when combined with the present disclosure and the data herein, the skilled artisan will to be able to express a mutant BEHAB protein or peptide in a cell or a mammal without undue experimentation.

One of skill in the art will appreciate that many methods exist for the expression of a protein or peptide in a cell or a mammal, including the introduction of a vector or expression vector comprising an isolated nucleic acid encoding the desired protein or peptide into a cell or mammal. The skilled artisan will further appreciate that a vector can comprise the isolated nucleic of SEQ ID NO:4, or some biologically active portion thereof.

The present invention also includes mimetopes of a mutant BEHAB protein and peptide of the present invention. As used herein, a mimetope of a mutant BEHAB protein or peptide refers to any compound that is able to mimic the activity of such a mutant BEHAB protein or peptide (e.g., ability to titrate a protease that cleaves BEHAB, thereby preventing the cleavage of native BEHAB), often because the mimetope has a structure that mimics the mutant BEHAB protein or peptide. It is to be noted, however, that the mimetope need not have a structure similar to an mutant BEHAB protein or peptide as long as the mimetope functionally mimics the protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); synthetic or natural organic or inorganic molecules, including nucleic acids; and/or any other peptidomimetic compounds. Mimetopes of the present invention can be designed using computer-generated structures of a mutant BEHAB protein or peptide of the present invention. Mimetopes can also be obtained by generating random samples of molecules, such as oligonucleotides, peptides or other organic molecules, and screening such samples by affinity chromatography techniques using the corresponding binding partner, (e.g., a protease that cleaves BEHAB or anti-BEHAB antibody). A preferred mimetope is a peptidomimetic compound that is structurally and/or functionally similar to a mutant BEHAB protein or peptide of the present invention, particularly to the cleavage site of the mutant BEHAB protein. Methods for generating mimetopes and peptidomimetics are well known in the art, and are detailed in, for example, Kazmierski (1999, Peptidomimetics Protocols (Methods in Molecular Medicine Vol. 23) Humana Press, Totowa N.J.).

The present invention also includes methods for inhibiting the expression and/or activity of BEHAB in a mammal. The skilled artisan will understand, when equipped with the present disclosure and the data disclosed herein, that higher levels of BEHAB expression increase tumor size and decrease survival rates in mammals afflicted with primary CNS tumors. That is, the data presented elsewhere herein demonstrate, for the first time, that mammals with primary CNS tumors overexpressing BEHAB have larger tumor volumes and shorter survival times when compared to mammals expressing normal levels of BEHAB, or to mammals expressing mutant BEHAB. Thus, the skilled artisan will certainly appreciate that a method of treating a primary CNS tumor encompasses inhibiting BEHAB expression.

An inhibitor of BEHAB expression and/or activity is administered to a mammal thereby decreasing BEHAB and providing a therapeutic benefit. The skilled artisan would appreciate, based upon the disclosure provided herein, that BEHAB can be inhibited using a wide plethora of techniques well-known in the art or to be developed in the future. That is, the invention encompasses inhibiting BEHAB expression, e.g., inhibition of transcription and/or translation. This is because, as demonstrated by the data disclosed elsewhere herein, reduced levels of BEHAB expression and/or activity mediated a variety of effects, including, but not limited to, decreased tumor size and increased survival rates. Thus, inhibiting BEHAB includes, but is not limited to, inhibiting translation and/or transcription of a nucleic acid encoding the protein.

Further, the routineer would understand, based upon the disclosure provided elsewhere herein, that inhibition of BEHAB includes, but is not limited to, inhibiting the biological activity of the molecule. This is because, as the data disclosed elsewhere herein demonstrate, inhibition of BEHAB activity, in that BEHAB is not cleaved by an endogenous protease, limits the progression of a primary CNS tumor. These data indicate that inhibition of BEHAB activity provides a therapeutic benefit for treatment of a disease, such as, but not limited to, primary CNS tumors, and the like.

The present invention encompasses inhibiting BEHAB by inhibiting expression of a nucleic acid encoding BEHAB. Methods for inhibiting the expression of a gene are well known to those of ordinary skill in the art, and include the use of ribozymes or antisense nucleic acid molecules.

Antisense nucleic acid molecules are DNA or RNA molecules that are complementary to some portion of an mRNA molecule. When present in a cell, antisense nucleic acids hybridize to an existing mRNA molecule and inhibit translation into a gene product. Inhibiting the expression of a gene using an antisense nucleic acid molecule is well known in the art (Marcus-Sekura, 1988, Anal. Biochem. 172:289), as are methods to express an antisense nucleic acid molecule in a cell (Inoue, 1993, U.S. Pat. No. 5,190, 931).

The invention encompasses inhibiting the expression of BEHAB using a ribozyme. Using ribozymes for inhibiting gene expression is well known to those of ordinary skill in the art (Cech et al., 1992, J. Biol. Chem. 267:17479–17482; Hampel et al., 1989, Biochemistry 28: 4929–4933; Altman et al., 1992, U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030–3034), allowing the selective cleavage of specific mRNA molecules. Given the nucleotide sequence of BEHAB is well known in the art (Hockfield et al., 1997, U.S. Pat. No. 5,635,370) one of ordinary skill in the art can synthesize an antisense polynucleotide or ribozyme without undue experimentation, provided with the disclosure and references incorporated herein.

The skilled artisan will further appreciate, when armed with the present disclosure and the data presented herein, that cleavage of BEHAB mediates progression of primary CNS tumors. While not wishing to be bound by any particular theory, it can be theorized that while BEHAB is normally expressed endogenously at low levels and does not necessarily cause primary CNS tumors during normal expression, the cleavage of BEHAB, or more specifically the products of the cleavage event mediate the progression of a primary CNS tumor in a mammal. Thereby, as will be recognized by one of skill in the art, inhibiting the activity of the BEHAB cleavage products can be used as a method of treating a mammal afflicted with a primary CNS tumor.

The invention also encompasses the use of pharmaceutical compositions of an appropriate antibody, protein or peptide, mimetope, peptidomimetic, and/or isolated nucleic acid to practice the methods of the invention, the compositions comprising an appropriate antibody, protein or peptide, mimetope, peptidomimetic, and/or isolated nucleic acid and a pharmaceutically-acceptable carrier.

As used herein, the term "pharmaceutically-acceptable carrier" means a chemical composition with which an appropriate antibody, protein or peptide, mimetope, peptidomimetic, and/or isolated nucleic acid may be combined and which, following the combination, can be used to administer the appropriate antibody, protein or peptide, mimetope, peptidomimetic, and/or isolated nucleic acid to a mammal.

The pharmaceutical compositions useful for practicing the invention may be administered to deliver a dose of between 1 ng/kg/day and 100 mg/kg/day. In one embodiment, the invention envisions administration of a dose which results in a concentration of the compound of the present invention between 1 $\mu$M and 10 $\mu$M in a mammal.

Pharmaceutical compositions that are useful in the methods of the invention may be administered systemically in oral solid formulations, ophthalmic, suppository, aerosol, topical or other similar formulations. They can be administered directly into the CNS intrathecally, intraventricularly, intraparenchymally, via direct injection, or via bioengineered polymers. In addition to the appropriate antibody, protein or peptide, mimetope, peptidomimetic, and/or isolated nucleic acid, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate hypericin derivative according to the methods of the invention.

Compounds which are identified using any of the methods described herein may be formulated and administered to a mammal for treatment of the diseases disclosed herein are now described.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to mammals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, rodents (including rats and mice), birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal, intraventricular, intraparenchymal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e.

powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution, suspension, or slow-release polymer. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Another formulation is the activate ingredient incorporated in a slow-release polymer. Such polymers are well known in the pharmaceutical arts, and are detailed in, for example, U.S. Pat. Nos. (4,728,512; 4,728,513; 5,084,287; 5,285,186).

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

A pharmaceutical composition of the invention can be prepared, packaged, or sold in a formulation suitable for direct CNS administration. Such formulations may, for example, be in the form of liquid administered by an Ommaya reservoir, by intrathecal or intraventricular administration, by direct intraparenchymal injection, by slow-release polymers, or other such methods well known in the pharmaceutical and neurological fields.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically dosages of the compound of the invention which may be administered to a mammal, preferably a human, range in amount from 1 μg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to a mammal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

B. Methods of Diagnosing a Primary CNS Tumor

The present invention further encompasses methods for the diagnosis of primary CNS tumors, other central nervous system tumors, and other neuropathological disorders relating to BEHAB, including, but not limited to, gliomas, well-differentiated astrocytomas, anaplastic astrocytomas, glioblastoma multiforme, ependymomas, oligodendrogliomas, ganglioneuromas, mixed gliomas, brain stem gliomas, optic nerve gliomas, meningiomas, pineal tumors, pituitary tumors, pituitary adenomas, primitive neuroectodermal tumors, schwannomas, vascular tumors, lymphomas, and the like. This is because, as demonstrated by the data disclosed elsewhere herein, BEHAB overexpression is highly correlated with the progression and invasiveness of primary CNS tumors and the like. The present invention therefore includes methods of determining the level of expression of BEHAB in a mammal, and therefore a method of diagnosing a primary CNS tumor. In all instances recited herein, whether treating or diagnosing a primary CNS tumor, the most preferred mammal is a human.

The invention includes a method of diagnosing a primary CNS tumor in a mammal. The method comprises obtaining a biological sample from a first mammal and comparing the level of BEHAB (expression, amount, activity) in that sample with the level of BEHAB in a sample obtained from a normal second mammal that is otherwise identical to the first mammal but which is not afflicted with a primary CNS tumor. A higher level of BEHAB in the sample from the first mammal compared with the level of BEHAB in the sample obtained from the second otherwise identical mammal not afflicted with a primary CNS tumor is an indication that the first mammal is afflicted with a primary CNS tumor. This is because, as disclosed elsewhere herein, an increased level of BEHAB expression is associated with, inter alia, larger tumor volumes and decreased survival rates.

The invention further includes a method of diagnosing primary CNS tumor progression in a mammal. As will be appreciated by the skilled artisan, once armed with the present disclosure and the data herein, BEHAB cleavage mediates the progression of brain tumors, resulting in, among other things, larger tumor volumes and decreased survival times. Therefore, the present invention includes a method of diagnosing brain tumor progression in a mammal. The method comprises obtaining a biological sample from a first mammal and comparing the level of BEHAB cleavage in that sample with the level of BEHAB cleavage in a sample obtained from a normal second mammal that is otherwise identical to the first mammal but which is not afflicted with a primary CNS tumor, or is afflicted with a primary CNS tumor that has not progressed as far as the primary CNS tumor in the second mammal, as can be easily determined by one of skill in the art using standard neurological indicators. A higher level of BEHAB cleavage in the sample from the first mammal compared with the level of BEHAB cleavage in the sample obtained from the second otherwise identical mammal is an indication that the first mammal is afflicted with a primary CNS tumor progressing at a higher rate. This is because, as disclosed elsewhere herein, an increased level of BEHAB cleavage is associated with larger tumor volumes and decreased survival rates, and the like.

One of skill in the art will appreciate, when armed with the present disclosure and data herein, that methods for determining the level of BEHAB cleavage include, but are not limited to Western blotting, ELISA, and other immunodetection assays well known in the art.

In one aspect, the biological sample is selected from the group consisting of a blood sample, a neurological tissue biopsy, a cerebrospinal fluid sample, urine, saliva, and the like.

The invention includes a method of assessing the effectiveness of a treatment for a primary CNS tumor in a mammal. The method comprises assessing the level of BEHAB expression, amount, and/or activity, before, during and after a specified course of treatment for a disease, disorder or condition mediated by or associated with increased BEHAB expression (e.g., primary CNS tumors and the like). This is because, as stated previously elsewhere herein, increased BEHAB expression, amount and/or activity is associated with or mediates larger tumor volumes and decreased animal survival rates, which is a feature of increased mortality due to primary CNS tumors.

Thus, assessing the effect of a course of treatment upon BEHAB expression/amount/activity indicates the efficacy of the treatment such that a lower level of BEHAB expression, amount, or activity indicates that the treatment method is successful.

The course of therapy to be assessed can include, but is not limited to, surgery, chemotherapy, radiation therapy, and/or the multiple modes of therapy for a primary CNS tumor disclosed herein.

The invention encompasses probes and primers for detecting the expression, amount, or activity of a BEHAB gene.

The skilled artisan, when equipped with the present disclosure and the data disclosed herein, will appreciate that probes are provided that are capable of specifically hybridizing to DNA or RNA of a BEHAB gene. For purposes of the present invention, probes are "capable of hybridizing" to DNA or RNA of BEHAB if they hybridize to a BEHAB gene under conditions of either high or moderate stringency, see Sambrook et al. (1989, Molecular Cloning: A Laboratory Manual, Cold Spring Harbor Laboratory, New York) but not significantly or detectably to an unrelated gene. Preferably, the probe hybridizes to suitable nucleotide sequences under high stringency conditions, such as hybridization in 5×SSPE, 1× Denhardt's solution, 0.1% SDS at 65° C., and at least one wash to remove unhybridized probe in the presence of 0.2×SSC, 1× Denhardt's solution, 0.1% SDS at 65° C. Except as otherwise provided herein, probe sequences are designed to allow hybridization to a BEHAB gene, but not to DNA or RNA sequences from other genes. The probes are used, for example, to hybridize to nucleic acid that is present in a biological sample, including, but not limited to, blood, cerebrospinal fluid, lymph, or tissue, isolated from a patient. The hybridized probe is then detected, thereby indicating the presence of the desired cellular nucleic acid. The skilled artisan will recognize that the cellular nucleic acid can be subjected to an amplification procedure, such as polymerase chain reaction (PCR), prior to hybridization. Alternatively, a BEHAB gene can be amplified and the amplified product subjected to DNA sequencing. A BEHAB gene can be detected by DNA sequence analysis or hybridization with a BEHAB specific oligonucleotide probe under conditions and for a time sufficient to allow hybridization to the specific allele. Typically, the hybridization buffer can contain tetramethyl ammonium chloride and the like, see Sambrook et al. (1989, Molecular Cloning: A Laboratory Manual, Cold Spring Harbor Laboratory, New York).

Nucleic acid probes of the present invention may be composed of either deoxyribonucleic acids (DNA), ribonucleic acids (RNA), nucleic acid analogues (e.g., peptide nucleic acids), or any combination thereof, and can be as few as about 12 nucleotides in length, usually about 14 to 18 nucleotides in length, and possibly as large as the entire sequence of a BEHAB gene. Selection of probe size is somewhat dependent upon the use of the probe, and is well within the skill of the art.

Suitable probes can be constructed and labeled using techniques that are well known in the art. Shorter probes of, for example, 12 bases can be generated synthetically and labeled with $^{32}P$ using $T_4$ polynucleotide kinase. Longer probes of about 75 bases to less than 1.5 kb are preferably generated by, for example, PCR amplification in the presence of labeled precursors such as, but not limited to, $[\alpha^{32}P]$ dCTP, digoxigenin-dUTP, or biotin-dATP. Probes of more than 1.5 kb are generally most easily amplified by transfecting a cell with a plasmid containing the relevant probe, growing the transfected cell into large quantities, and purifying the relevant sequence from the transfected cells, see Sambrook et al. (1989, Molecular Cloning: A Laboratory Manual, Cold Spring Harbor Laboratory, New York).

Probes can be labeled by a variety of markers, including for example, radioactive markers, fluorescent markers, enzymatic markers, and chromogenic markers. The use of $^{32}P$ is but one example for marking or labeling a particular probe.

It is a feature of this aspect of the invention that the probes can be utilized to detect the presence of a BEHAB mRNA or DNA within a sample. However, if the relevant sample is present in only a limited number, then it can be beneficial to amplify the relevant sequence so that it may be more readily detected or obtained.

A variety of methods may be utilized in order to amplify a selected sequence, including, for example, RNA amplification (see Lizardi et al., 1988 Bio/Technology 6:1197–1202; Kramer et al., 1989, Nature 339:401–402; Lomeli et al., 1989, Clinical Chem. 35:1826–1831; U.S. Pat. No. 4,786,600), and DNA amplification utilizing ligase chain reaction (LCR) or PCR (U.S. Pat. Nos. 4,683,195, 4,683,202, and 4,800,159) (see also U.S. Pat. Nos. 4,876,187 and 5,011,769, which describe an alternative detection/amplification system comprising the use of scissile linkages), or other nucleic acid amplification procedures that are well within the level of ordinary skill in the art. With respect to PCR, for example, the method can be modified as known in the art. Transcriptional enhancement of PCR can be accomplished by incorporation of bacteriophage T7 RNA polymerase promoter sequences in one of the primary oligonucleotides, and immunoenzymatic detection of the products from the enhanced emitter may be effected using anti-RNA:DNA antibodies (Blais, 1994, Appl. Environ. Microbiol. 60:348–352). PCR can also be used in combination with reverse dot-blot hybridization (Iida et al., 1993, FEMS Microbiol. Lett. 114:167–172). PCR products may be quantitatively analyzed by incorporation of dUTP (Duplaa et al., 1993, Anal. Biochem. 212:229–236), and samples may be filter sampled for PCR-gene probe detection (Bej et al., 1991, Appl. Environ. Microbiol. 57:3529–3534).

The invention encompasses a method of detecting BEHAB overexpression and therefore diagnosing a primary CNS tumor wherein PCR amplification is used to detect BEHAB DNA. As an example, a DNA sample is denatured at about 92° to about 95° C. in order to generate single-stranded DNA. The DNA sample can be a cDNA generated from RNA. Specific primers are then annealed to the single-stranded DNA at about 37° C. to about 70° C., depending on the proportion of AT/GC in the primers and other factors well known in the art. The primers are extended at about 72° C. with, for example, Taq DNA polymerase or another thermostable DNA polymerase in order to generate the opposite strand to the template. These steps constitute one cycle, which can be repeated in order to amplify the selected sequence. For greater specificity, nested PCR can be performed. In nested PCR, a second amplification is performed using a second set of primers derived from sequences within the first amplified product. The entire coding region of BEHAB may be amplified from, for example, cDNA using an adequate number of primers to generate fragment lengths that are a convenient size for determining their sequence. The number of primers necessary will be well known to one of skill in the art.

The present invention further includes a method wherein, LCR amplification is utilized for amplification. LCR primers can be synthesized such that the 5' base of the upstream primer is capable of hybridizing to a unique base pair in a desired gene to specifically detect a BEHAB gene.

Within an embodiment of the present invention, the probes can be used in an automated, non-isotopic strategy wherein target nucleic acid sequences are amplified by PCR, and then desired products are determined by, for example, a calorimetric oligonucleotide ligation assay (OLA) (Nickerson et al., 1990, Proc. Natl. Acad. Sci. USA 81:8923–8927).

Primers for the amplification of a selected sequence should be selected from sequences that are highly specific to BEHAB and form stable duplexes with the target sequence. As is well known in the art, the primers should also be non-complementary, especially at the 3' end, should not form dimers with themselves or other primers, and should not form secondary structures or duplexes with other regions of DNA. In general, primers of about 18 to about 20 nucleotides are preferred, and can be easily synthesized using techniques well known in the art. PCR products, and other nucleic acid amplification products, may be quantitated using techniques well known in the art (Duplaa et al., 1993, Anal. Biochem. 212:229–236; Higuchi et al., 1993, Bio/Technology 11:1026–1030).

The skilled artisan will readily understand, when armed with the present disclosure and the data disclosed herein, that diagnostics can be developed which are capable of detecting the overexpression of BEHAB nucleic acid in a mammal. This is because, as demonstrated by the data elsewhere herein, increased expression of BEHAB in a mammal, when compared to a mammal with normal endogenous BEHAB expression or a mammal with overexpression of a non-cleavable BEHAB mutant, results in larger tumors and decreased survival time. Thereby, determining the level of BEHAB expression in a mammal or cell can be used as a powerful and novel diagnostic technique for the detection of among other things, a primary CNS tumor, and the like.

C. Methods of Identifying Useful Compounds

The present invention further includes a method of identifying a compound that affects expression of BEHAB in a cell. The method comprises contacting a cell with a test compound and comparing the level of expression of BEHAB in the cell so contacted with the level of expression of BEHAB in an otherwise identical cell not contacted with the compound. If the level of expression of BEHAB is higher or lower in the cell contacted with the test compound compared to the level of expression of BEHAB in the otherwise identical cell not contacted with the test compound, this is an indication that the test compound affects expression of BEHAB in a cell.

The invention encompasses methods to identify a compound that affects expression of BEHAB. One skilled in the art would appreciate, based upon the disclosure provided herein, that assessing the level of BEHAB can be performed using probes (e.g., antibodies and/or nucleic acid probes that specifically bind with of BEHAB), such that the method can identify a compound that selectively affects expression of BEHAB. Such compounds are useful for inhibiting expression of BEHAB. One skilled in the art would understand that such compounds can be useful for inhibiting a disease, disorder, or condition mediated by and/or associated with increased expression of BEHAB, e.g., increased levels of BEHAB is associated with primary CNS tumors, and BEHAB expression is associated with increased tumor volume and decreased survival rates. Thus, the skilled artisan would appreciate, based on the disclosure provided herein, that it may useful to decrease expression of BEHAB.

Similarly, the present invention includes a method of identifying a compound that reduces expression of BEHAB in a cell. The method comprises contacting a cell with a test compound and comparing the level of expression of BEHAB in the cell contacted with the compound with the level of expression of BEHAB in an otherwise identical cell, which is not contacted with the compound. If the level of expression of BEHAB is lower in the cell contacted with the compound compared to the level in the cell that was not contacted with the compound, then that is an indication that the test compound reduces expression of BEHAB in a cell.

The invention also includes a method of identifying a compound that decreases cleavage of BEHAB in a cell. The method comprises contacting a cell with a test compound and comparing the level of BEHAB cleavage in the cell contacted with the compound with the level of BEHAB cleavage in an otherwise identical cell, which is not contacted with the compound. If the level of BEHAB cleavage is lower in the cell contacted with the compound compared to the level in the cell that was not contacted with the compound, then that is an indication that the test compound decreases cleavage of BEHAB in a cell.

A compound that decreases BEHAB cleavage in a cell is useful since it has been demonstrated herein that BEHAB cleavage is associated with primary CNS tumor progression and invasiveness. Additionally, the data disclosed herein demonstrate that BEHAB cleavage mediates or is associated with larger tumor volumes and decreased animal survival rates. Thus, methods of identifying a compound that decreases BEHAB cleavage can be used to treat various diseases, including, but not limited to, primary CNS tumors.

The skilled artisan will further appreciate that the present invention is not limited to a method of identifying a useful compound in a cell or an animal. That is, the present invention includes methods of identifying a useful compound in a cell-free system. A cell-free system, as used herein, refers to an in vitro assay wherein the components necessary for a reaction to take place are present, but are not associated with a cell. Such components can include cellular enzymes, transcription factors, proteins, nucleic acids, and the like, provided that they are substantially free from a cell. As disclosed by the data herein, BEHAB cleavage assays can be performed free of a cell or animal, including the use of immunoprecipitation assays and the like. Thereby, the present invention includes a method of identifying a useful compound for treating a primary CNS tumor in a cell-free system.

One skilled in the art would appreciate, based on the disclosure provided herein, that the level of expression of BEHAB in the cell may be measured by determining the level of expression of mRNA encoding BEHAB. Alternatively, the level of expression and/or cleavage of BEHAB can be determined by using immunological methods to assess BEHAB production and cleavage, as exemplified herein using Western blot analysis using anti-BEHAB antibodies. Further, nucleic acid-based detection methods, such as Northern blot and PCR assays and the like, can be used as well. In addition, the level of BEHAB activity and/or cleavage in a cell can also be assessed by determining the level of various parameters which can be affected by BEHAB activity and/or cleavage, such as, for example, tumor volume, tumor invasiveness, and animal survival rates. Thus, one skilled in the art would appreciate, based upon the disclosure and reduction to practice provided herein, that there are a multitude of methods that are well-known in the art which can be used to asses the level of BEHAB activity and cleavage in a cell including those disclosed herein and others which may be developed in the future.

In addition, a protein that specifically binds with BEHAB or its cleavage products, e.g. a receptor or other BEHAB-associated protein, can be identified using, for example, a yeast two hybrid assay. Yeast two hybrid assay methods are well-known in the art and can be performed using well documented techniques, for example those described in Bartel and Fields, (The Yeast Two-Hybrid System, Oxford University Press, Cary, N.C.). Therefore, once armed with the teachings provided herein, e.g., the full amino and nucleic acid sequences of the BEHAB protein, one skilled in the art can easily identify a protein that specifically binds with BEHAB or its cleavage products such as, but not limited to, a BEHAB target or receptor protein.

One skilled in the art would understand, based upon the disclosure provided herein, that the invention encompasses any molecule identified using the methods discussed elsewhere herein. That is, molecules that associate with BEHAB, such as but not limited to, a BEHAB receptor protein, or a BEHAB target protein, can be used to develop therapeutics and diagnostics for diseases, disorders or conditions mediated by BEHAB cleavage product interaction with a BEHAB-associated protein such as primary CNS tumors, gliomas, well-differentiated astrocytomas, anaplastic astrocytomas, glioblastoma multiforme, ependymomas, oligodendrogliomas, ganglioneuromas, mixed gliomas, brain stem gliomas, optic nerve gliomas, meningiomas, pineal tumors, pituitary tumors, pituitary adenomas, primitive neuroectodermal tumors, schwannomas, vascular tumors, and lymphomas. That is, one skilled in the art would appreciate, as more fully set forth elsewhere herein in discussing antibodies that specifically bind with BEHAB, that a BEHAB-associated protein can be used to develop therapeutics that inhibit BEHAB cleavage product activity in a cell by inhibiting BEHAB cleavage product receptor/ligand interactions and other BEHAB binding interactions.

BEHAB-associated proteins identified by the above-disclosed methods can be used directly to inhibit BEHAB interactions by contacting a cell with the BEHAB-associated protein, or a portion thereof, or they can be used to develop antibodies and/or peptidomimetics that can inhibit the BEHAB-associated protein interaction with BEHAB thereby inhibiting BEHAB function, activity, and cleavage. Thus, BEHAB-associated proteins, including a BEHAB receptor proteins or BEHAB cleavage product proteins, are useful and are encompassed by the invention.

VII. Kits

The present invention encompasses various kits which comprise a compound, including a nucleic acid encoding mutant BEHAB, a mutant BEHAB polypeptide, an antibody that specifically binds BEHAB, a nucleic acid complementary to a nucleic acid encoding BEHAB but in an antisense orientation, an antibody to BEHAB cleavage products, an applicator, and instructional materials which describe use of the compound to perform the methods of the invention. Although model kits are described below, the contents of other useful kits will be apparent to the skilled artisan in light of the present disclosure. Each of these kits is contemplated within the present invention.

In one aspect, the invention includes a kit for treating a primary CNS tumor. The kit is used in the same manner as the methods disclosed herein for the present invention. Briefly, the kit may be used to contact a cell with a nucleic acid encoding a mutant BEHAB molecule of the invention. Additionally, the kit comprises an applicator and an instructional material for the use of the kit. These instructions simply embody the examples provided herein.

The kit further includes a pharmaceutically-acceptable carrier. The composition is provided in an appropriate amount as set forth elsewhere herein. Further, the route of administration and the frequency of administration are as previously set forth elsewhere herein.

In another aspect, the invention includes a kit for treating a primary CNS tumor. The kit is used in the same manner as the methods disclosed herein for the present invention. Briefly, the kit may be used to contact a cell with a mutant BEHAB polypeptide molecule of the invention. Additionally, the kit comprises an applicator and an instructional material for the use of the kit. These instructions simply embody the examples provided herein. The kit further includes a pharmaceutically-acceptable carrier. The composition is provided in an appropriate amount as set forth elsewhere herein. Further, the route of administration and the frequency of administration are as previously set forth elsewhere herein.

The invention further encompasses a kit for the treatment of a primary CNS tumor. The skilled artisan will appreciate that the kit can be used according to the methods set forth herein. The kit comprises an antibody, small molecule, or peptide that binds BEHAB, or some fragment thereof, an applicator, and an instructional material substantially similar to the examples provided herein. The kit further includes a pharmaceutically acceptable carrier, of which the composition, route of administration, and frequency of administration are as previously disclosed elsewhere herein.

Further, the invention comprises a kit comprising an antisense nucleic acid complementary to a nucleic acid encoding a mammalian BEHAB molecule, or some fragment thereof. Such kits can be used according to the methods of the invention to mediate the decreased expression of BEHAB. Additionally, the kit comprises an applicator and an instructional material for the use of the kit. These instructions simply embody the examples provided herein. The kit further includes a pharmaceutically-acceptable carrier. The antisense nucleic acid and pharmaceutically-acceptable carrier are provided in an appropriate amount as set forth elsewhere herein. Further, the route of administration and the frequency of administration are as previously set forth elsewhere herein.

The present invention further encompasses a kit for the treatment of a primary CNS tumor. Briefly, the kit comprises an antibody, a small molecule, or a peptide that specifically binds to BEHAB cleavage products, or some fragment thereof, and can be used according to the methods set forth elsewhere herein. The kit of the invention further comprises an applicator and an instructional material, similar to the methods set forth herein, for the use of the kit. The kit also comprises a pharmaceutically-acceptable carrier, of which the composition, route and frequency of administration, and dosage are set forth previously herein.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

The materials and methods used in the experiments presented in this Example are now described.

Site-Directed Mutagenesis: Full-length BEHAB cDNA was cloned into the EcoR1 site of the eukaryotic expression vector pCDNA3 (Invitrogen, Carlsbad, Calif.) as described in Zhang et al. (1998, Journal of Neuroscience 18: 2370–2376). The full-length BEHAB expression vector was mutated using the QUIKCHANGE site-directed mutagenesis kit following the manufacturer's protocol (Stratagene, La Jolla, Calif.). Incorporation of the appropriate mutation was confirmed by sequencing using the fluorescently-labelled dideoxynucleotide chain termination method.

Cell Culture and Transfections: CNS-1 cells (American Type Culture Collection, Manassas, Va.) were grown and maintained in RPMI with 10% fetal calf serum (FCS). Cells were split (1:6 to 1:10) and re-plated every four days. 75% confluent cells were plated in 60 mm tissue culture plates and transfected using 4 µg of the appropriate expression construct and Fugene 6 according to the manufacturer's protocol (Roche, Indianapolis, Ind.). Briefly, DNA and Fugene 6 were incubated with cells in their standard media for six hours, after which the media was removed and replaced with fresh media overnight. The following day, cells were selected for expression of the transgene with G-418 (80 µg/µl, Invitrogen). Stable pools of transfected cells were derived by maintaining cells in G-418-supplemented media for two and a half weeks. After selection, stably transfected pools of cells were maintained in media containing G-418 at a concentration of (40 µg/µl).

In vitro proliferation and cell death assays: The effects of transfections on cell proliferation and cell death were evaluated. For both assays, cells were grown in 96 well tissue culture plates with an initial plating density of $4 \times 10^4$ cells per well in 200 µl of media. Cell proliferation was measured by cellular uptake of MTT (3,-[4,5-dimethylthiazol-2-yl]-2, 5-diphenyltetrazolium bromide; Sigma Chemical Co., St. Louis, Mo.). Briefly, 100 µl of media was removed was removed and saved for the cell death assays. 25 µl of MTT (2 mg/ml in Dulbecco's phosphate buffered saline; DPBS) was added to the remaining cells and media and incubated for 3 hours at 37° C. in a humidified incubator (5% $CO_2$ in air). 100 µl of 40 mM hydrochloric acid in isopropanol was added to solubilize the resultant product and samples were incubated at 37° C. for 2 hours. Samples were analyzed in quadruplicate by measuring the absorbance at 550 nM using a microplate reader.

100 µl of cell-free media was used for the cell death assays. The media was assayed for lactate dehydrogenase (LDH) activity using the Cytotoxicity Detection Kit per the manufacturer's instructions (Roche, Indianapolis, Ind.). Briefly, media was incubated with lactate, which is oxidized to pyruvate by LDH and reduces $NAD^+$ to NADH. NADH in the presence of diaphorase catalyzes the conversion of yellow tetrazolium salt into red formazan salt. Samples were analyzed in quadruplicate by measuring the absorbance at 450 nM using a microplate reader.

Animal Studies: Female Lewis rats (Charles River Laboratories, Wilmington, Mass.) were anesthetized (75 mg/kg ketamine, 5 mg/kg xylazine) and positioned in a stereotaxic instrument (David Kopf Instruments, Tujunga, Calif.) with the incisor bar set at 3.0 mm below the intraaural line. About 70%–80% confluent CNS-1 cells were harvested from 100 mm tissue culture plates using trypsin. Cells were washed once in DPBS and suspended in phosphate buffered saline (PBS) supplemented with 1 µg/µl $MgCl_2$, 1 µg/µl $CaCl_2$, and 0.1% glucose at a concentration of $5 \times 10^4$ cells/µl, except for the survival curve with the inhibitor in which the concentration of cells was $1 \times 10^5$ cells/µl. Intrathalamic injections were made using a 10 µl Hamilton syringe fitted with a 26 gauge beveled needle into the right thalamus at the coordinates 2.8 mm posterior to bregma, 2.2 mm lateral to the midline, and 5.0 mm ventral to the dura. A total volume of 3 µl of the cell suspension was injected over 3 minutes and the needle was left in place for an additional minute before slow withdrawal.

The health and survival rate of the animals was evaluated every six hours. Animals that were not able to right themselves within 15 seconds of being placed on their side were considered to have reached the survival endpoint and sacrificed. The day of sacrifice was recorded as the last day of survival.

Histology: Rats were deeply anesthetized and transcardially perfused with PBS followed by ice-cold 4% PBS-paraformaldehyde. 40 µM frozen sections were sliced on a cryostat and brains from animals implanted with transfected CNS-1 cells were sliced coronally. Every fifth section was stained with cresyl violet for estimation of tumor volumes.

Image Analysis and Tumor Volume Estimation: Tissue sections were analyzed using NIH Image (a publicly available program accessible from the National Institutes of Health website). Tumor areas were defined manually on every fifth section through the tumor by a researcher blinded to the experimental conditions. Tumor volumes were reconstructed using Calvalieri's estimator of morphometric volume (Rosen and Harry, 1990, Journal of Neuroscience Methods 35: 115–124).

Electrophoresis and Western Analysis: Samples were electrophoresed on 8% SDS-PAGE gels and proteins were then electrophoretically transferred to nitrocellulose (Laemmli et al., 1970, Nature 227:680–685; Towbin et al., 1979, Proc. Natl. Acad. Sci. U.S.A. 76:4350–4354). Blots were incubated with rabbit affinity purified antisera (1:10, 000) or B50 (1:5000) (Matthews et al., 2000, J. Biol. Chem. 275: 22695–22703) followed by alkaline phosphatase-conjugated goat anti-rabbit IgG secondary antibody (1:4000, Jackson ImmunoResearch Labs, West Grove, Pa.). Immunoreactive bands were visualized with nitro blue tetrazolium and 5-bromo-4-chloro-3-indoyl phosphate.

Statistical Analysis: The significance of comparisons between animals implanted with transfected cell lines was determined by one-way analysis of variance (ANOVA). Results from the in vitro proliferation and cell death assays were analyzed using a 4×7 (cell line×day) repeated measures ANOVA.

The results of the experiments presented in this Example are now described.

The Effect of the NVY Mutation on BEHAB Cleavage: To study the role of BEHAB cleavage in primary CNS tumors, a construct was generated that blocked or inhibited BEHAB cleavage. The effect of mutating the BEHAB $Glu^{395}$-$Ser^{396}$ cleavage site on cleavage of the full length protein was examined. Previous work on aggrecan, which has a cleavage site very similar to the BEHAB $Glu^{395}$-$Ser^{396}$ site, showed that mutation of the three amino acids just downstream of the cleavage site from ARG to NVY completely blocked cleavage (Fosang et al., 2000, J. Biol. Chem. 275: 33027–33037). Therefore, using site-directed mutagenesis, the effect of the NVY mutation on BEHAB cleavage was examined. This mutation changed the amino acid cleavage site from $^{393}$Glu-Ser-Glu-Ser-Arg-Gly$^{398}$ to $^{393}$Glu-Ser-Glu-Asn-Val-Tyr$^{398}$ (SEQ ID NO:1 and SEQ ID NO:2, respectively). To evaluate the effect of the NVY mutation on BEHAB cleavage, CNS-1 cells were transiently transfected with either full-length BEHAB, or with the mutated BEHAB construct and the resultant protein was analyzed by Western blot with the B6 and B50 antibodies (specifically binding the C-terminus and the neo-epitope formed by BEHAB cleavage, respectively, Matthews et al., 2000. J. Biol. Chem. 275: 22695–22703).

Cells transiently transfected with both the normal and mutated BEHAB produced the full-length product as shown with the B6 antibody (FIG. 1A). Normal full-length BEHAB was cleaved at the $^{393}$Glu-Ser-Glu-Ser-Arg-Gly$^{398}$ (SEQ ID NO:1) cleavage site as shown with the B50 antibody. In sharp contrast, while a large amount of full-length protein was made by cells transfected with the NVY mutant construct, no cleavage was detected (FIG. 1A). To determine if the NVY mutated form of BEHAB was completely incapable of being cleaved, samples were immunoprecipitated with the B50 antibody to detect trace amount so cleavage product. Even with this higher sensitivity assay, no reactive product was detected, indicating that the NVY mutation completely inhibited cleavage of the full-length protein.

Figure 1B:
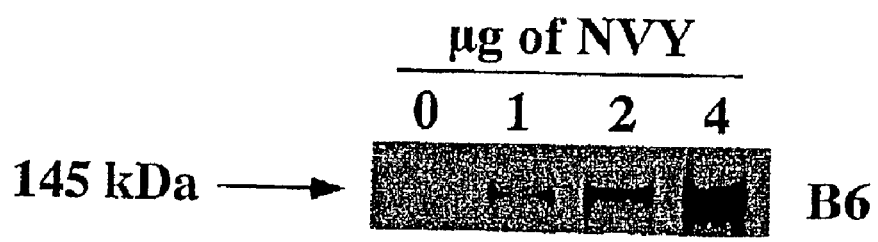

The effect of the NVY mutation on cleavage of BEHAB was further investigated by co-transfecting CNS-1 cells with the normal full-length BEHAB and NVY constructs. These experiments were designed to determine if the NVY mutant BEHAB could inhibit cleavage of the normal substrate. Cells were co-transfected with 2 µg of the normal BEHAB expression construct and either 0, 1, 2, or 4 µg of the mutated BEHAB construct. While the addition of the NVY mutant construct increased the amount of full-length BEHAB, it had no effect on the ability of the protease to cleave the normal BEHAB protein (FIG. 1B). These results suggest that, although not wishing to be bound by any particular theory, while the mutated form of BEHAB is itself uncleavable, it does not necessarily inhibit the protease.

Figure 1C:
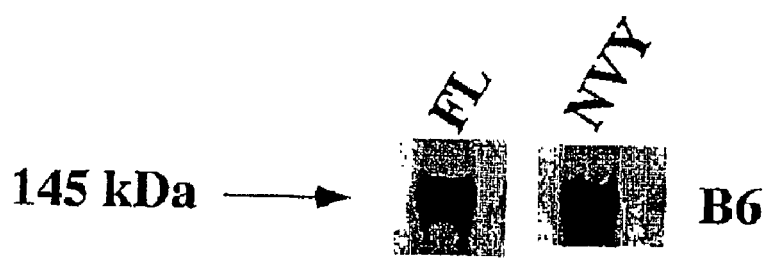

The Effect of the NVY Mutant on Cell Proliferation and Cell Death:

To evaluate the effects of the NVY cleavage site mutation of BEHAB on cell proliferation and cell death, CNS-1 cells were stably transfected with either a green fluorescent protein (GFP) expression vector (CNS-1-GFP), the normal BEHAB expression vector (CNS-1-FL), or the NVY mutated vector (CNS-1-NVY). Pools of stably transfected cells were selected in G418 and analyzed as described above. As observed using transient transfections, pools of CNS-1-NVY cells made full-length BEHAB, but did not cleave it (FIG. 1C).

Figure 2A:
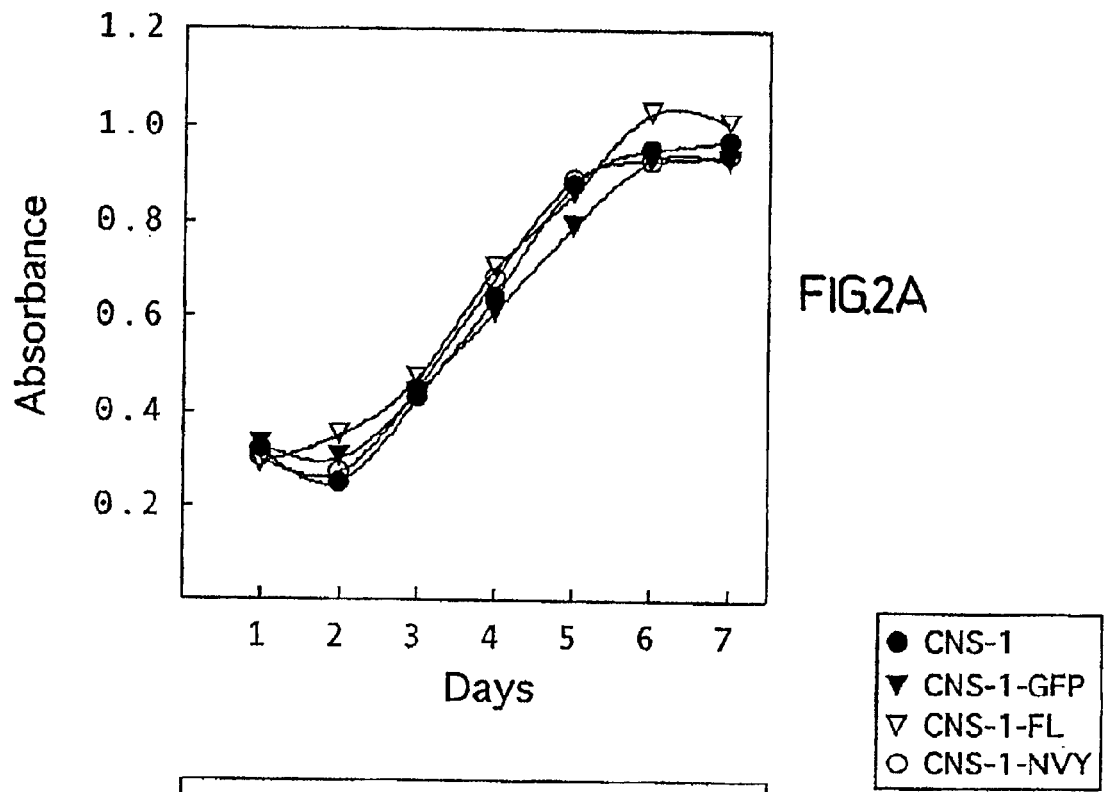
FIGS. 2A and 2B, depicts the effects of stable transfection on cell proliferation and cell death. CNS-1-FL, CNS-1-GFP, and CNS-1-NVY stable cell lines were compared to parental CNS-1 cells for the effect of CNS-1-FL, CNS-1-GFP, and CNS-1-NVY transfection on cell proliferation (FIG. 2A) and cell death (FIG. 2B).

Cell proliferation was analyzed in vitro on stably transfected cells using an MTT assay. MTT is converted to a dye by the succinate-tetrazolium reductase system, an enzyme system of the mitochondrial respiratory chain, thereby providing a measure of the number of viable cells. Proliferation was evaluated over seven days. There were no differences in cell proliferation in any of the transfected cells (FIG. 2A). Furthermore, none of the transfected pools showed any differences from the non-transfected parental CNS-1 cells.

Figure 2B:
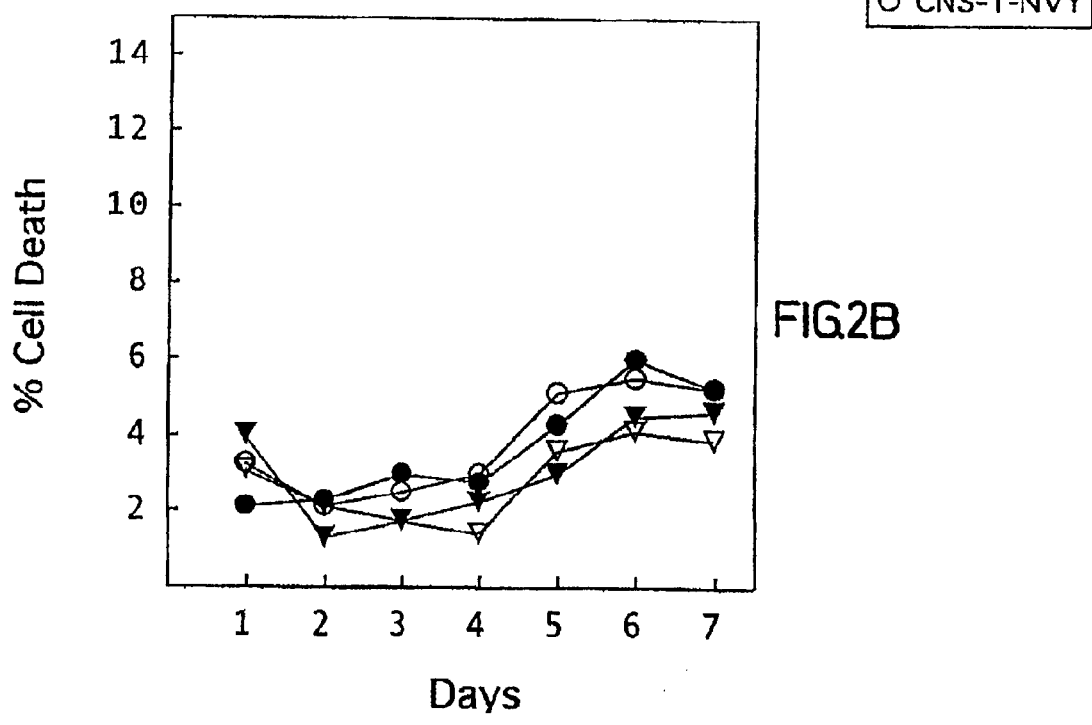
Figure 3A:
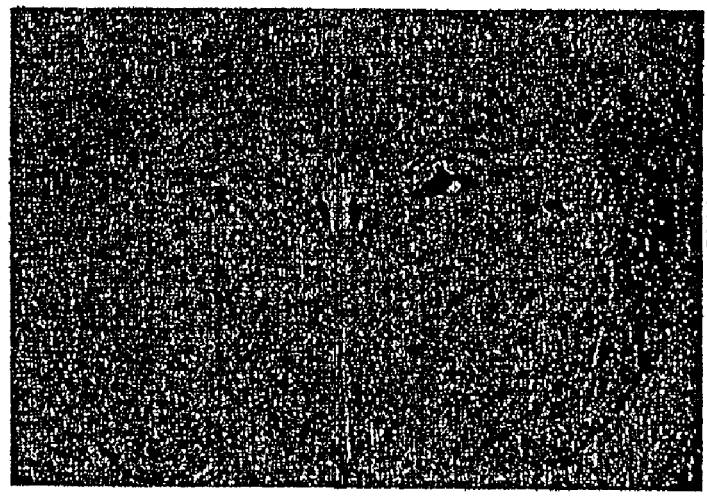
FIGS. 3A through 3D, depicts the effect of transfection using CNS-1-FL, CNS-1-GFP, and CNS-1-NVY on tumor volume. Stably transfected cells were implanted intracranially in rats for eight days, and the relative sizes of tumors that resulted were evaluated histologically.
Figure 3B:
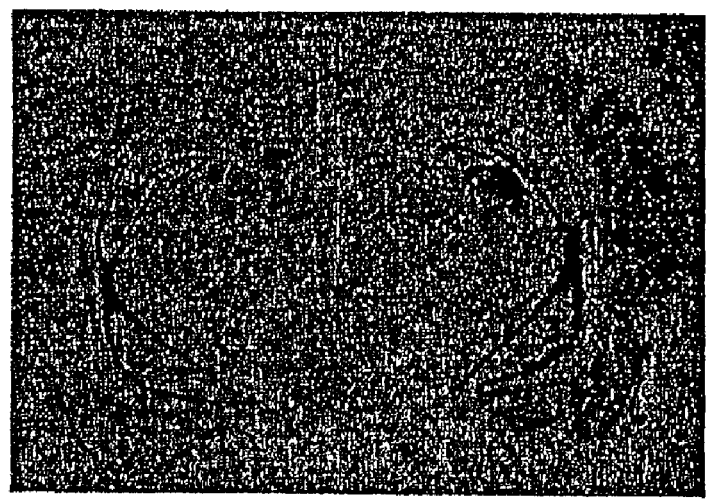
Figure 3C:
Figure 3D:
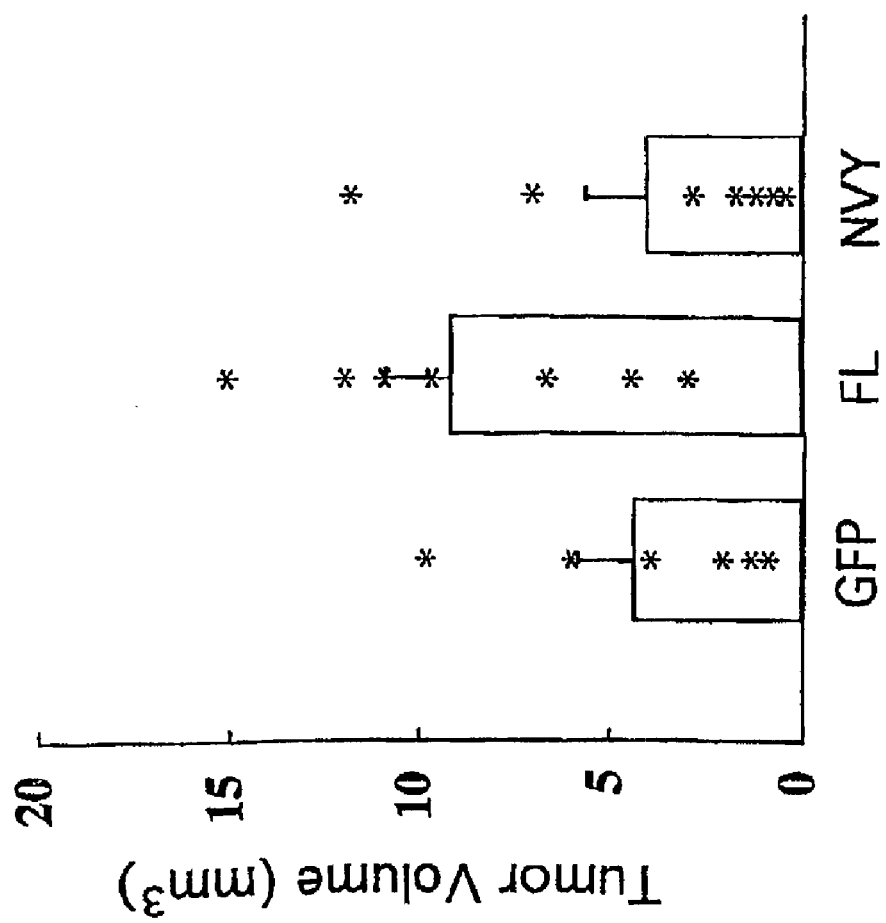

Cell death was evaluated using the LDH assay. LDH is an enzyme present normally only in the cytoplasm. LDH activity was measured in the media, where LDH would only be present if released by dead or dying cells. There was a low level of about 2% to about 3% cell death over the first four days in all cell lines. Cell death increased slightly on every subsequent day, however, there were no differences in the percent dell death between any cell line at any time point (FIG. 2B). Therefore, while the mutated construct is uncleavable, it has no apparent effect on cell proliferation or death in vitro.

The NVY Uncleavable BEHAB Does Not Affect the Phenotype of CNS-1 Tumors: Previous studies have indicated that CNS-1 cells transfected with the normal full-length BEHAB form larger tumors than GFP transfected controls. However, in 9L cells, which neither produce nor cleave BEHAB, transfection with full-length BEHAB does not change the phenotype of the tumors (Zhang et al., 1998, J. of Neuroscience 18: 2370–2376). To investigate the role of BEHAB cleavage in tumor progression, pools of CNS-1 cells stably transfected with the expression vectors described above were grown as intracranial grafts. Eight days after tumor implantation, animals (n=8) were perfused and their brains processed for histology. Every fifth section was stained with cresyl violet and tumor areas were estimated by image analysis. Volumes were reconstructed from these analyses. Consistent with previous results, CNS-1-FL tumors were larger and more infiltrative than CNS-GFP. 2–5 CNS-1-NVY tumors were not significantly different in size from CNS-1-GFP tumors. Importantly however, CNS-1-NVY tumors were significantly smaller than CNS-1-FL tumors (Table 1, FIG. 3). While not wishing to bound by any particular theory, these results demonstrate that production of BEHAB alone is insufficient to increase tumor progression, but cleavage of the full-length protein plays a critical role in this process.

Figure 4:
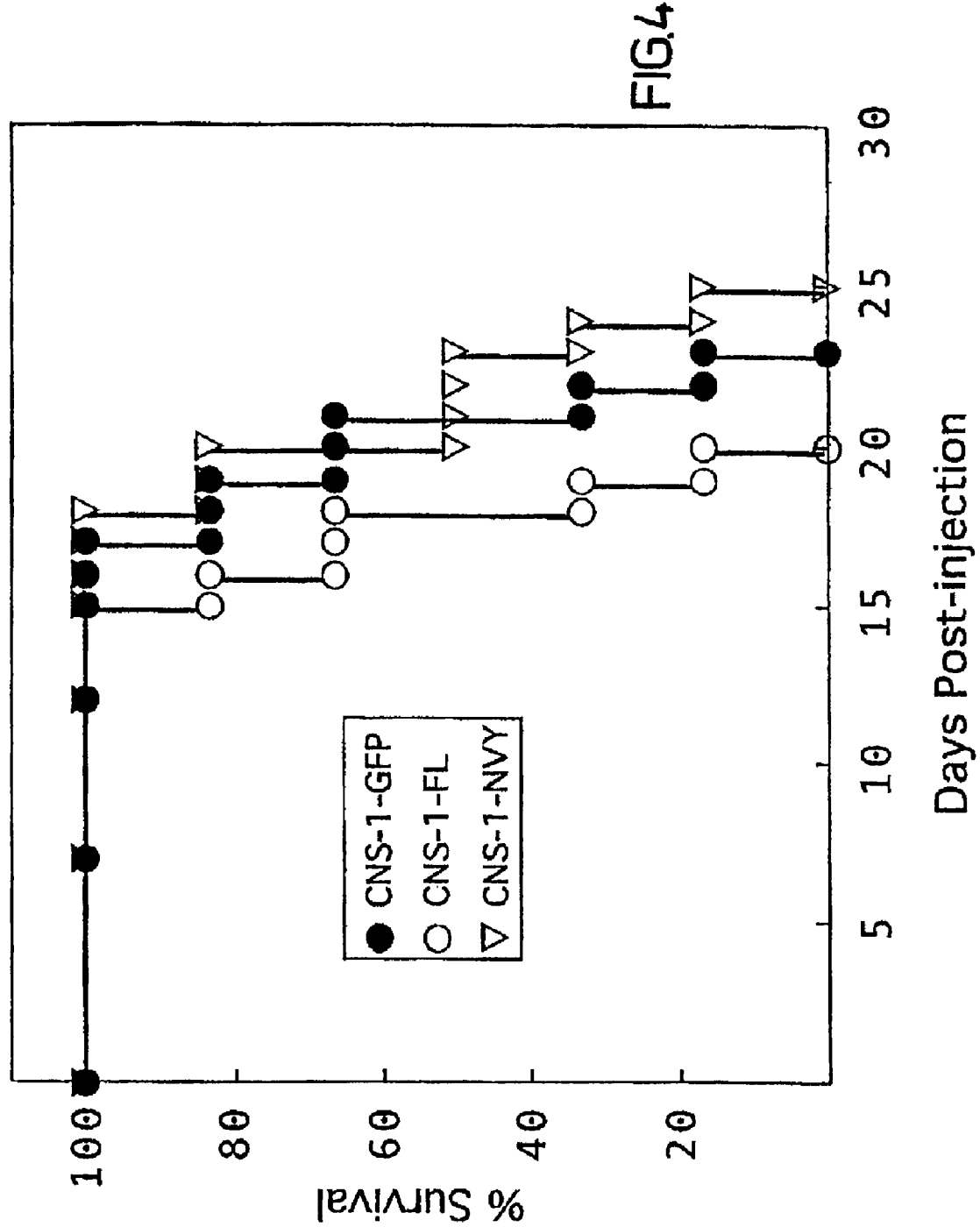
FIG. 4 is a graph depicting the effect of tumors derived from cells stably transfected with CNS-1-FL, CNS-1-GFP, and CNS-1-NVY on animal survival. Animals with CNS-1-FL tumors survived a significantly shorter time than animals with CNS-1-GFP tumors or CNS-1-NVY tumors. Survival in animals with CNS-1-NVY tumors was not significantly different from survival in animals with CNS-1-GFP control tumors.

To further investigate the effects of mutated BEHAB on tumor progression, the effect of the mutant BEHAB construct on animal (n=6) survival was investigated. It was previously discovered that CNS-1-FL tumors decrease animal survival (Nutt et al., 2001, Cancer Res. 61: 7056–7059). Consistent with these results, animals implanted with CNS-1-FL tumors reached the survival endpoint an average of three days earlier than animals implanted with CNS-1-GFP tumors. However, CNS-1-NVY implanted animals did not reach the survival endpoint faster than controls. In fact, animals with CNS-1-NVY tumors survived slightly longer than animals implanted with CNS-1-GFP, although with the number of animals in this study to date, the difference is not significant. CNS-1-NVY implanted animals survived an average of four days longer than CNS-1-FL implanted animals, a 23% increase in survival (Table 1, FIG. 4).

TABLE 1

| Tumor Type | Tumor Volume in mm$^3$ | Significance Compared to CNS-1-FL | Survival in Days | Sigificance Compared to CNS-1-FL |
| --- | --- | --- | --- | --- |
| CNS-1-FL | 9.2 ± 4.3 | | 17.6 ± 0.76 | |
| CNS-1-GFP | 4.4 ± 3.4 | $p < 0.05$ | 20.5 ± 0.88 | $p < 0.05$ |
| CNS-1-NVY | 4.0 ± 4.2 | $p < 0.05$ | 21.6 ± 1.1 | $p < 0.05$ |

Discussion

Previous work has demonstrated that the 9L gliosarcoma cell line, which grows as a non-invasive tumor, becomes invasive when transfected with a 5' fragment of BEHAB (Zhang et al., 1998, J. Neuroscience 18: 2370–2376). However, transfection of 9L cells with full-length BEHAB does not change the tumor phenotype from wild type 9L cells. In sharp contrast, CNS-1 cells transfected with full-length BEHAB increase the size and invasiveness of tumors. The difference in phenotype of the different cell lines is explained by differences in the ability of these two cell lines to cleave BEHAB. CNS-1 cells cleave the full-length protein at the Glu$^{395}$-Ser$^{396}$ cleavage site, creating 90 kDa and 50 kDa fragments. In contrast, 9L cells do not proteolytically process the full-length protein. Additionally, previous studies showed that BEHAB cleavage in the CNS-1 cells is mediated by ADAMTS-4 (Matthews et al., 2000, J. Biol. Chem. 275: 22695–22703). The role of BEHAB cleavage in glioma progression was evaluated using CNS-1 cells transfected with a mutated, uncleavable, form of BEHAB. The effects of this construct on tumor progression and animal survival were studied, and for the first time firmly demonstrate the role of BEHAB cleavage in the progression of gliomas.

Mutation of BEHAB/brevican cleavage site from $^{393}$Glu-Ser-Glu-Ser-Arg-Gly$^{398}$ to $^{393}$Glu-Ser-Glu-Asn-Val-Tyr$^{398}$ (SEQ ID NO 1 and SEQ ID NO:2, respectively) made the protein completely uncleavable by CNS-1 cells. Importantly, this uncleavable mutant had a different effect than the normal full-length construct on rat CNS-1 tumors. While CNS-1-FL tumors were larger and decreased the survival time of animals relative to animals with control tumors, CNS-1-NVY tumors were not phenotypically distinguishable from the control tumors. These studies clearly demonstrate the critical role that both cleavage and processing play in BEHAB function in primary CNS tumors.

CNS-1-NVY tumors were smaller than CNS-1-FL tumors, but phenotypically similar to control tumors. This result is informative about the mechanism of BEHAB cleavage-mediated effects in gliomas, especially in light of the fact that CNS-1 cells are induced to express endogenous BEHAB when grown in the brain. Accordingly, all three of the cell lines used in these experiments express normal levels of endogenous BEHAB; CNS-1-FL tumors express, in addition to endogenous BEHAB, exogenous BEHAB in a cleavable form; and CNS-1-NVY tumors express, in addition to endogenous BEHAB, exogenous BEHAB in an uncleavable form. Therefore, if the NVY mutant was working as a dominant negative in CNS-1 cell tumors, it would be expected that the CNS-1-NVY tumors would be significantly smaller than the control tumors (CNS-1-GFP) by disrupting the normal function of the BEHAB, which is not the case. Rather, it appears that the CNS-1-NVY tumors have instead have been transfected with a molecule that produces no change in their phenotype compared to control tumors, strongly suggesting that the cleavage products of BEHAB mediate unique interactions and/or functions not mediated by the full-length protein. As an example, if BEHAB cleavage products simply solublized the matrix and allowed cell movement, the production of uncleavable BEHAB would counteract this effect. However, tumors with or without the uncleavable substrate seem to be very similar. These results suggest that BEHAB cleavage products have a unique function that is not mediated by the full-length protein itself. The data evident herein demonstrate that BEHAB cleavage potentiates the progression of primary CNS tumors and that inhibiting BEHAB cleavage can reduce tumor progression. These studies strongly indicate that inhibition of BEHAB cleavage may represent an important new therapeutic strategy, and therefore inhibition of BEHAB cleavage or the function of the cleavage products will serve as an effective and novel method for treating primary CNS tumors.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. An isolated nucleic acid encoding a mammalian mutant BEHAB (Brain Enriched Hyaluronan Binding) molecule, wherein said isolated nucleic acid comprises the nucleic acid sequence set for in SEQ ID NO:4.

2. An isolated nucleic acid encoding a mammalian mutant BEHAB molecule, wherein said isolated nucleic acid has at least 99.8% identity to the nucleic acid sequence set forth in SEQ ID NO:4.

3. An isolated nucleic acid encoding a mammalian mutant BEHAB molecule, wherein the amino acid sequence of said mammalian mutant BEHAB molecule comprises the amino acid sequence set forth in SEQ ID NO:3.

4. The isolated nucleic acid of claim 1, said nucleic acid further comprising a nucleic acid encoding a tag polypeptide covalently linked thereto.

5. The isolated nucleic acid of claim 4, wherein said tag polypeptide is selected from the group consisting of a myc tag polypeptide, a glutathione-S-transferase tag polypeptide, a green fluorescent protein tag polypeptide, a myc-pyruvate kinase tag polypeptide, a $His_6$ tag polypeptide, an influenza virus hemagglutinin tag polypeptide, a flag tag polypeptide, and a maltose binding protein tag polypeptide.

6. The isolated nucleic acid of claim 1, said nucleic acid further comprising a nucleic acid specifying a promoter/regulatory sequence operably linked thereto.

7. A vector comprising the isolated nucleic acid of claim 1.

8. The vector of claim 7, said vector further comprising a nucleic acid specifying a promoter/regulatory sequence operably linked thereto.

9. A recombinant cell comprising the isolated nucleic acid of claim 1.

10. A recombinant cell comprising the vector of claim 7.

11. An isolated nucleic acid which is the full complement to an isolated nucleic acid encoding a mammalian BEHAB molecule, said nucleic acid which is the full complement being in an antisense orientation to the sequence set forth in SEQ ID NO:5.

12. The isolated nucleic acid of claim 11, wherein said nucleic acid is at least about 99.8% complementary to the nucleic acid which is the full complement sequence set forth in SEQ ID NO:5.

13. A recombinant cell comprising the isolated nucleic acid of claim 11.

14. A vector comprising the isolated nucleic acid of claim 11.

* * * * *